(12) United States Patent
Van Liere

(10) Patent No.: US 11,213,280 B2
(45) Date of Patent: Jan. 4, 2022

(54) BIOPSY DEVICE HAVING A LINEAR MOTOR DRIVE

(71) Applicant: C. R. Bard, Inc., Franklin Lakes, NJ (US)

(72) Inventor: Chad Van Liere, Phoenix, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 426 days.

(21) Appl. No.: 16/463,103

(22) PCT Filed: Nov. 28, 2017

(86) PCT No.: PCT/US2017/063427
§ 371 (c)(1),
(2) Date: May 22, 2019

(87) PCT Pub. No.: WO2018/111531
PCT Pub. Date: Jun. 21, 2018

(65) Prior Publication Data
US 2019/0365361 A1 Dec. 5, 2019

Related U.S. Application Data

(60) Provisional application No. 62/434,704, filed on Dec. 15, 2016.

(51) Int. Cl.
*A61B 10/02* (2006.01)
(52) U.S. Cl.
CPC .. *A61B 10/0275* (2013.01); *A61B 2010/0208* (2013.01)

(58) Field of Classification Search
CPC .................... A61B 10/0275; A61B 2010/0208
See application file for complete search history.

(56) References Cited

U.S. PATENT DOCUMENTS 4,881,551 A * 11/1989 Taylor ................ A61B 10/0275
600/567
4,907,599 A * 3/1990 Taylor ................ A61B 10/0275
600/567

(Continued)

FOREIGN PATENT DOCUMENTS

WO 9624289 A2 8/1996
WO 2008024684 A2 2/2008

*Primary Examiner* — Sean P Dougherty
(74) *Attorney, Agent, or Firm* — Dinsmore & Shohl LLP

(57) ABSTRACT

A biopsy device includes a first cannula driver connected to a first cannula and a second cannula driver connected to a second cannula. The first cannula driver has a first rack member and a flange. The second cannula driver has a second rack member. A drive assembly has a linear motor drive, a transmission assembly, a switching motor drive, and an electrical controller circuit. The electrical controller circuit is configured to execute program instructions to selectively operate the linear motor drive and the switching motor drive. The transmission assembly has a gear assembly drivably coupled to the switching motor drive and configured to releasably engage at least one of the first rack member of the first cannula driver and the second rack member of the second cannula driver. A coupler member is connected to the linear motor drive, and is configured to engage the flange of the first cannula driver.

20 Claims, 11 Drawing Sheets

(56) References Cited

U.S. PATENT DOCUMENTS

| | | | | |
|---|---|---|---|---|
| 4,940,061 | A * | 7/1990 | Terwilliger | A61B 10/0275 600/567 |
| 4,958,625 | A * | 9/1990 | Bates | A61B 10/0275 600/562 |
| 5,146,921 | A * | 9/1992 | Terwilliger | A61B 10/0275 600/567 |
| 5,243,994 | A * | 9/1993 | Ranalletta | A61B 10/0241 600/567 |
| 5,249,583 | A * | 10/1993 | Mallaby | A61B 10/0275 600/567 |
| 5,526,822 | A | 6/1996 | Burbank et al. | |
| 5,769,086 | A | 6/1998 | Ritchart et al. | |
| 5,830,153 | A | 11/1998 | Kass | |
| 6,261,241 | B1 * | 7/2001 | Burbank | A61B 10/0266 600/564 |
| 6,592,530 | B1 | 7/2003 | Farhadi | |
| 6,594,517 | B1 | 7/2003 | Nevo | |
| 7,022,085 | B2 * | 4/2006 | Cooke | A61B 10/0275 600/564 |
| 7,963,928 | B2 * | 6/2011 | Krause | A61B 10/0275 600/562 |
| 8,172,790 | B2 | 5/2012 | Hunter et al. | |
| 8,277,393 | B2 | 10/2012 | Miller et al. | |
| 8,398,583 | B2 | 3/2013 | Hunter et al. | |
| 8,480,595 | B2 * | 7/2013 | Speeg | A61B 10/0275 600/568 |
| 9,125,990 | B2 | 9/2015 | Hunter et al. | |
| 9,414,815 | B2 * | 8/2016 | Miller | A61B 10/0266 |
| 10,085,727 | B2 * | 10/2018 | Linderman | A61B 10/0283 |
| 2012/0109007 | A1 | 5/2012 | Rhad et al. | |
| 2015/0025505 | A1 | 1/2015 | Hunter et al. | |
| 2015/0088031 | A1 | 3/2015 | Paronetto | |

* cited by examiner

BIOPSY DEVICE HAVING A LINEAR MOTOR DRIVE

CROSS-REFERENCE TO RELATED APPLICATIONS

This application is a U.S. national phase of International Application No. PCT/US2017/063427, filed Nov. 28, 2017, which claims priority to U.S. provisional patent application Ser. No. 62/434,704, entitled "BIOPSY DEVICE HAVING A LINEAR MOTOR DRIVE" filed Dec. 15, 2016, each of which is incorporated herein by reference.

TECHNICAL FIELD

The present invention relates to biopsy devices, and, more particularly, to a biopsy device having a linear motor drive.

BACKGROUND ART

A biopsy may be performed on a patient to help in determining whether the cells in a biopsied region are cancerous. One type of biopsy device for performing a biopsy includes a hand-held driver assembly having an electromechanical driver that is attachable to a disposable biopsy probe assembly. The disposable biopsy probe assembly typically includes a stylet having a sample notch, and a cutting cannula coaxial with the stylet and movable relative to the stylet to selectively cover and uncover the sample notch. During a piercing operation, the cutting cannula and the stylet are retracted by operation of at least one rotary motor, and then released to fire forward by the motive force provided by one or more firing springs. Similarly, during a sample operation, the cutting cannula is retracted by operation of at least one rotary motor to expose the sample notch of the stylet, and then released to fire forward by the motive force provided by one or more firing springs to cover the sample notch and sever a tissue sample from surrounding tissue. Particularly during a firing operation, the spring-loaded components move forward to impact a mechanical stop, resulting in significant noise.

What is needed in the art is a biopsy device having a linear motor drive that operates in conjunction with electromechanical components to reduce or eliminate the impact between movable components, thereby providing a noise reduction of the biopsy device.

SUMMARY OF INVENTION

The present invention provides a biopsy device having a linear motor drive that operates in conjunction with electromechanical components to reduce or eliminate the impact between movable components, thereby providing a noise reduction of the biopsy device.

The invention in one form is directed to a biopsy device including a disposable needle assembly having a first cannula, a second cannula, a first cannula driver, and a second cannula driver. The first cannula driver is connected to a first portion of the first cannula. The second cannula driver is connected to a first portion of the second cannula. The first cannula driver has a first rack member and a flange connected to the first rack member. The second cannula driver has a second rack member. A drive assembly has a power source, a linear motor drive having at least one linear motor, a transmission assembly, a switching motor drive having at least one DC motor, and an electrical controller circuit. The power source is configured to supply electrical power to each of the linear motor drive, the switching motor drive, and the electrical controller circuit. The electrical controller circuit is configured to execute program instructions to selectively operate the linear motor drive and the switching motor drive. The transmission assembly has a gear assembly drivably coupled to the switching motor drive. The gear assembly is configured to releasably engage at least one of the first rack member of the first cannula driver and the second rack member of the second cannula driver. A coupler member is connected to the linear motor drive. The coupler member is configured to engage the flange of the first cannula driver.

The invention in another form is directed to a biopsy device including a disposable needle assembly having a cutting cannula, a stylet, a cannula driver, and a stylet driver. The cannula driver is connected to a first portion of the cutting cannula. The stylet driver is connected to a first portion of the stylet. The cannula driver has a first rack member and a flange connected to the first rack member. The stylet driver has a second rack member. A linear motor drive has at least one linear motor. A coupler member is connected to the linear motor drive. The coupler member is configured to engage the flange of the cannula driver of the disposable needle assembly. A switching motor drive has at least one rotary motor. A transmission assembly has a gear assembly drivably coupled to the switching motor drive. The gear assembly is configured to releasably engage at least one of the first rack member of the cannula driver and the second rack member of the stylet driver. An electrical controller circuit is configured to execute program instructions to selectively operate the linear motor drive and the switching motor drive.

An advantage of the present invention is that by using one or more linear motors to replace the firing springs associated with propelling the cutting cannula or the stylet or both forward, component impact is reduced or eliminated, yielding significant noise reduction.

Another advantage is that by using one or more linear motors to control linear displacement of the cutting cannula and stylet, virtually any combination of linear movements of the cutting cannula and the stylet, alone or in combination, is possible.

Yet another advantage is that by using one or more linear motors to move the cutting cannula relative to the stylet, the exposed extent of the sample notch of the stylet can be precisely controlled, so as to provide a continuous range of possible sample size openings at the sample notch.

BRIEF DESCRIPTION OF DRAWINGS

The above-mentioned and other features and advantages of this invention, and the manner of attaining them, will become more apparent, and the invention will be better understood by reference to the following description of an embodiment of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
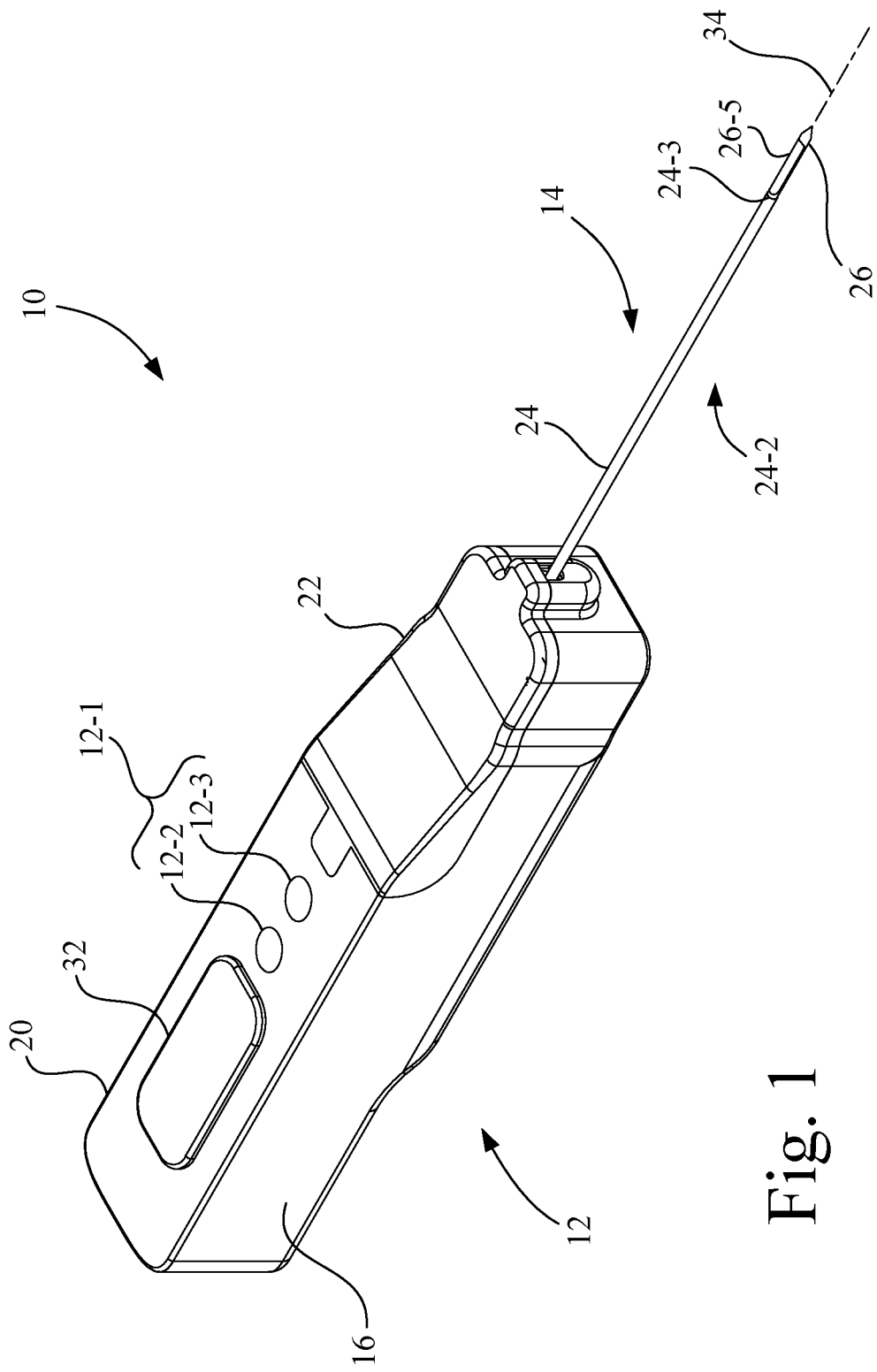
FIG. 1 is a perspective view of a biopsy device having a driver assembly and a disposable biopsy needle assembly, in accordance with the present invention.
Figure 2:
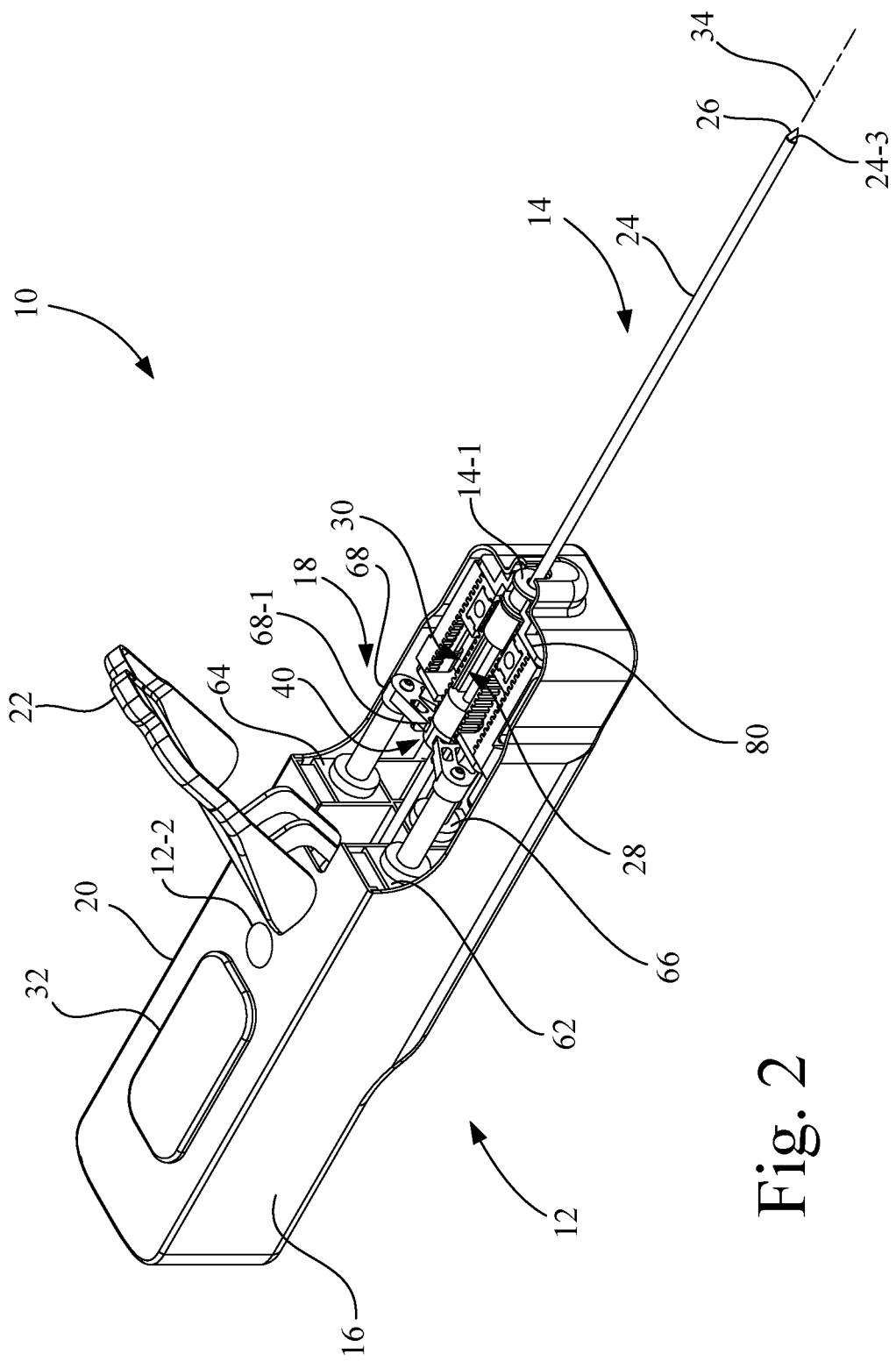
FIG. 2 is a perspective view of a biopsy device of FIG. 1, with a door opened to expose a portion of the electromechanical drive assembly of the driver assembly.

Referring now to the drawings, and more particularly to FIGS. 1 and 2, there is shown a biopsy device 10 which generally includes a driver assembly 12 and a disposable biopsy needle assembly 14. In the present embodiment, driver assembly 12 may be reusable on multiple patients, whereas disposable biopsy needle assembly 14 is used only on a single patient. As used herein, the term "disposable" refers to a device that is intended for use with one patient only, and is discarded after use.

As shown in FIG. 1, driver assembly 12 includes a user interface circuit 12-1. User interface circuit 12-1 is configured to receive a user input and generate a corresponding user output signal that is supplied to controller components of driver assembly 12. In the present embodiment, user interface circuit 12-1 may be a simple touch pad having a plurality of control buttons, individually identified as prime-pierce button 12-2 and sample button 12-3. Alternatively, it is contemplated that user interface circuit 12-1 may be a digital touch screen display.

Driver assembly 12 includes a housing 16 defining an internal receptacle 18 (see FIG. 2) for receiving and mounting disposable biopsy needle assembly 14. In the present embodiment, driver assembly 12 may include a removable panel 20 to facilitate reception of disposable biopsy needle assembly 14. Panel 20 may include a hinged door 22 for permitting access to the various drives contained in driver assembly 12.

Figure 3:
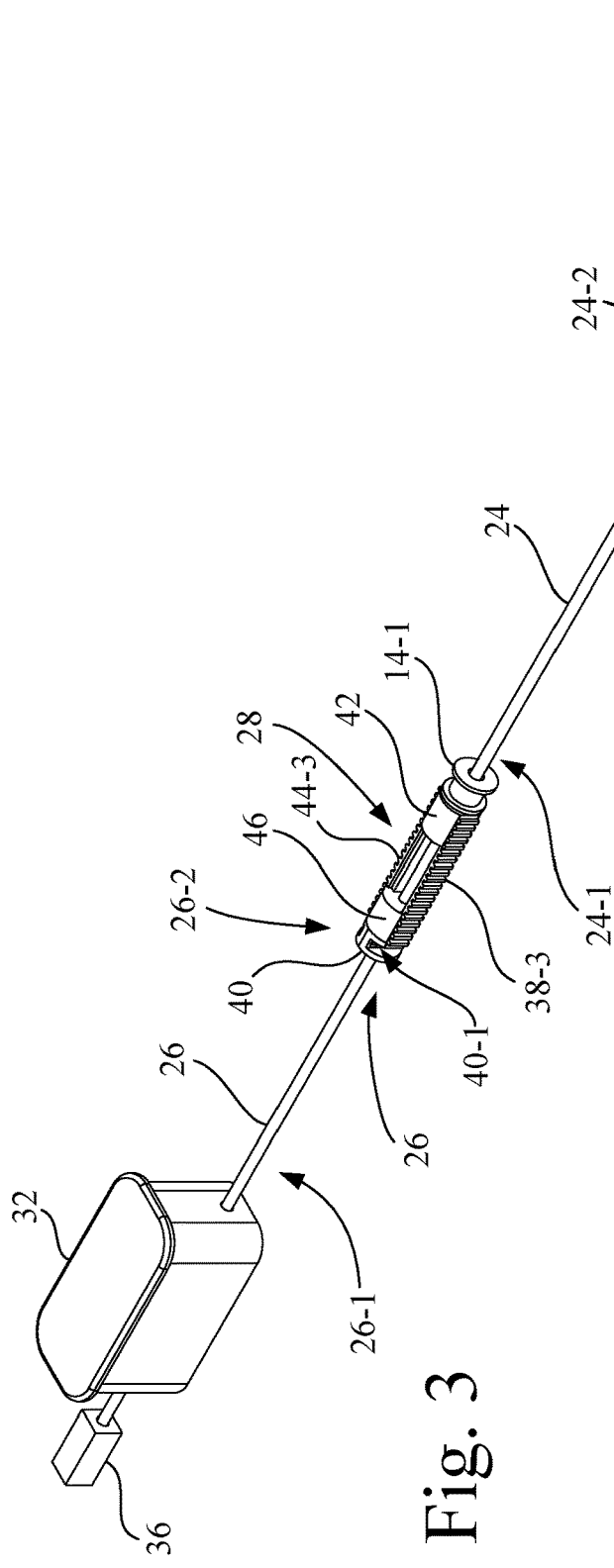
FIG. 3 is a perspective view of the disposable biopsy needle assembly, which is shown coupled to a vacuum source of the driver assembly.
Figure 4:
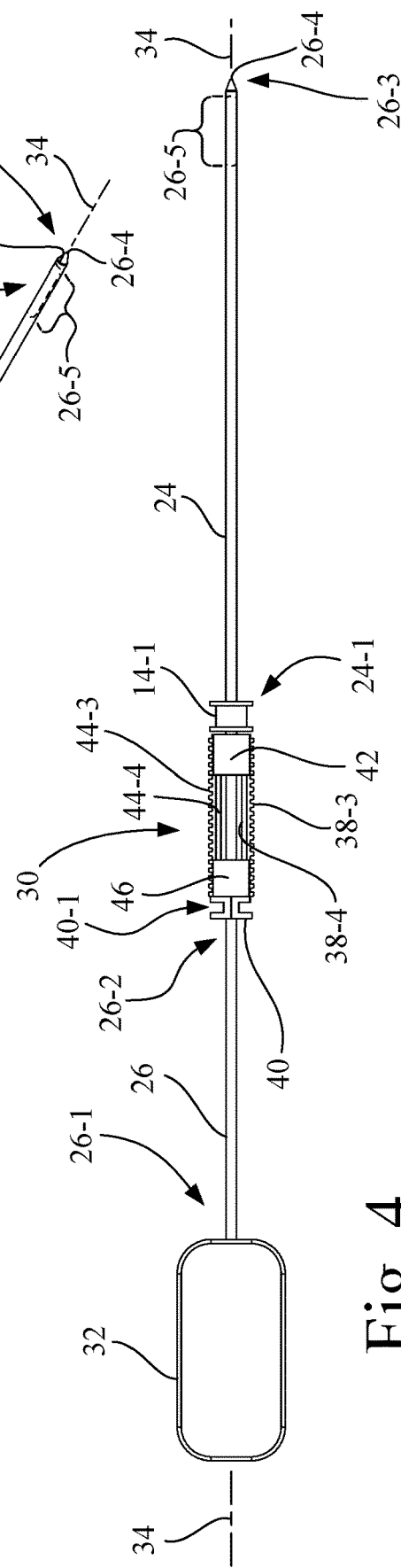
FIG. 4 is a top view of the disposable biopsy needle assembly of FIG. 3, showing the cutting cannula driver and stylet driver of the disposable biopsy needle assembly.

Referring also to FIGS. 3 and 4, disposable biopsy needle assembly 14 includes a cutting cannula 24, a stylet 26, a cutting cannula driver 28, a stylet driver 30, and a sample receptacle 32, each of which is arranged along a longitudinal axis 34. FIG. 1 shows cutting cannula 24 in a retracted position relative to stylet 26, and FIG. 2 shows both cutting cannula 24 and stylet 26 in the extended position. Disposable biopsy needle assembly 14 also includes a front alignment bushing 14-1 through which cutting cannula 24 and stylet 26 coaxially extend. Front alignment bushing 14-1 is received in a front portion of housing 16 of driver assembly 12, as shown in FIG. 2.

In the present embodiment, cutting cannula 24 is an outer cannula that is coaxial with stylet 26 with respect to longitudinal axis 34. Cutting cannula 24 has a proximal end portion 24-1 and a distal end portion 24-2 having an annular cutting edge 24-3.

Stylet 26 is an inner cannula having a proximal end portion 26-1, a central portion 26-2, and a closed distal end portion 26-3 having a piercing tip 26-4, and a sample notch 26-5 (shown in dashed lines as being covered by cutting cannula 24). The proximal end portion 26-1 of stylet 26 is slidably coupled to sample receptacle 32. A lumen of stylet 26, and in turn sample notch 26-5, is in fluid communication with sample receptacle 32. Also, shown in FIG. 3 is a vacuum source 36, which is contained in housing 16 of driver assembly 12. Vacuum source 36 may be, for example, a vacuum pump (e.g., a diaphragm vacuum pump) that is connected in fluid communication with sample receptacle 32, which when actuated generates a vacuum in stylet 26 to draw tissue into sample notch 26-5 and to transport a severed tissue sample through the lumen of stylet 26 and into sample receptacle 32.

Figure 5:
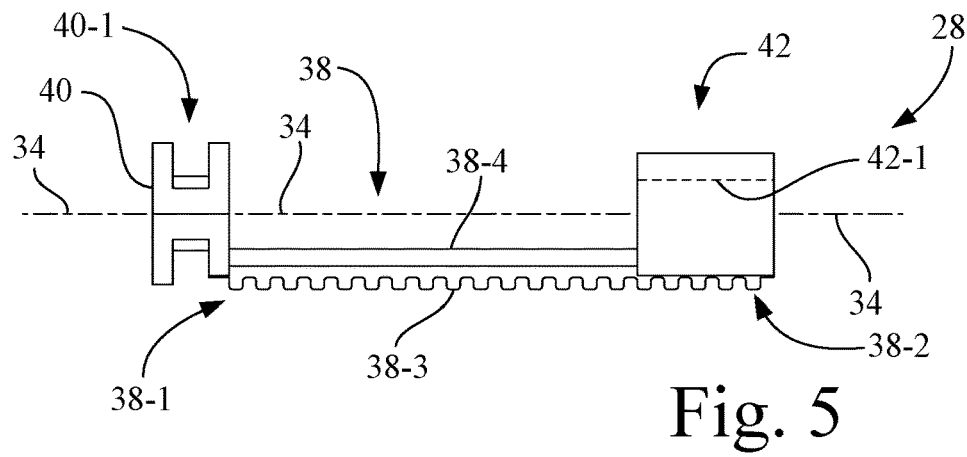
FIG. 5 is a top view of the cutting cannula driver of FIG. 4, in isolation.
Figure 7:
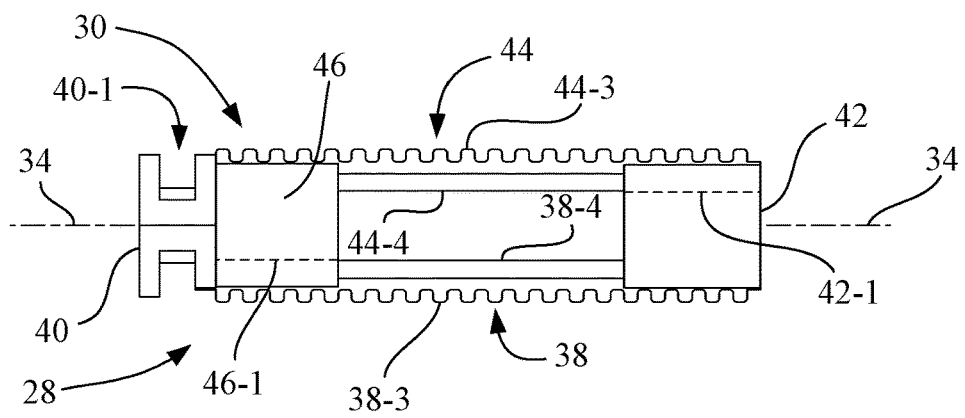
FIG. 7 is a top view of an assembly of the cutting cannula driver and the stylet driver of FIGS. 5 and 6, with the cutting cannula driver and the stylet driver being in a home position.
Figure 8:
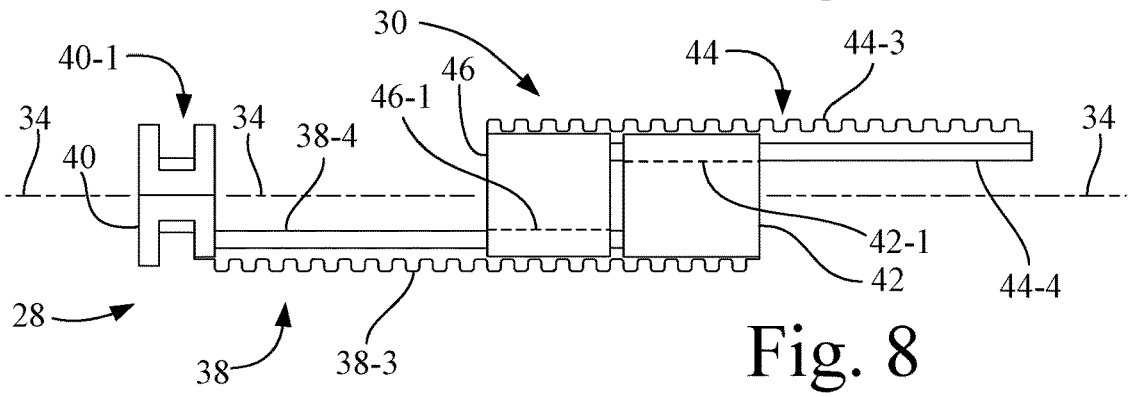
FIG. 8 is a top view of an assembly of the cutting cannula driver and the stylet driver of FIGS. 5 and 6, with the cutting cannula driver moved relative to the stylet driver.

Referring also to FIGS. 5, 7, and 8, cutting cannula driver 28 may be molded as a unitary plastic structure. Cutting cannula driver 28 is connected, e.g., via overmolding, to a first portion, e.g., proximal end portion 24-1, of the cutting cannula 24. (See also FIG. 3). Cutting cannula driver 28 has a first rack member 38, a flange 40, and a guide head 42. First rack member 38 has a proximal end 38-1, a distal end 38-2, an outwardly facing rack gear 38-3, and an inwardly facing rail 38-4. First rack member 38 has a longitudinal extent, and with the outwardly facing rack gear 38-3, i.e., a linear gear, extending along the longitudinal extent of the first rack member 38. Flange 40 has a drive slot 40-1. Flange 40 is connected to the proximal end 38-1 of first rack member 38. Guide head 42 is connected, e.g., formed, at the distal end 38-2 of first rack member 38. Guide head 42 has an inwardly facing slot 42-1 arranged parallel to the longitudinal axis. On an interior side of first rack member 38, opposite to outwardly facing rack gear 38-3, is inwardly facing rail 38-4. Inwardly facing rail 38-4 has a longitudinal extent that is parallel to the longitudinal extent of outwardly facing rack gear 38-3. Each of flange 40 and guide head 42 is positioned to be intersected by longitudinal axis 34. First rack member 38, including outwardly facing rack gear 38-3 and inwardly facing rail 38-4, is offset from longitudinal axis 34.

Figure 6:
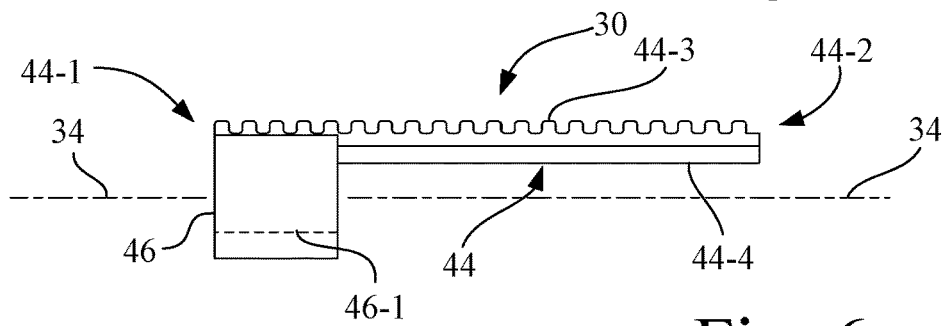
FIG. 6 is a top view of the stylet driver of FIG. 4, in isolation.

Referring also to FIGS. 6, 7, and 8, stylet driver 30 may be molded as a unitary plastic structure. Stylet driver 30 is connected, e.g., via overmolding, to a portion, e.g., central portion 26-2, of the stylet 26. Stylet driver 30 has a second rack member 44 and a guide head 46. Second rack member 44 has a proximal end 44-1, a distal end 44-2, an outwardly facing rack gear 44-3, and an inwardly facing rail 44-4. Second rack member 44 has a longitudinal extent, and with the outwardly facing rack gear 44-3, i.e., a linear gear, extending along the longitudinal extent of the second rack member 44. Guide head 46 is connected, e.g., formed, at the proximal end 44-1 of second rack member 44. Guide head 46 has an inwardly facing slot 46-1 arranged parallel to the longitudinal axis. On an interior side of second rack member 44, opposite to outwardly facing rack gear 44-3, is inwardly facing rail 44-4. Inwardly facing rail 44-4 has a longitudinal extent that is parallel to the longitudinal extent of outwardly facing rack gear 44-3. Guide head 46 is positioned to be intersected by longitudinal axis 34. Second rack member 44, including outwardly facing rack gear 44-3 and inwardly facing rail 44-4, is offset from longitudinal axis 34.

Referring to FIGS. 3-8, during assembly of disposable biopsy needle assembly 14, stylet 26 is received in the lumen of cutting cannula 24 along longitudinal axis 34. Inwardly facing rail 38-4 of cutting cannula driver 28 is radially aligned with the inwardly facing slot 46-1 of guide head 46 of stylet driver 30. Likewise, inwardly facing rail 44-4 of stylet driver 30 is radially aligned with inwardly facing slot 42-1 of guide head 42 of cutting cannula driver 28. Thereafter, inwardly facing rail 38-4 of cutting cannula driver 28 and inwardly facing rail 44-4 of stylet driver 30 are simultaneously and respectively slidably received in inwardly facing slot 46-1 of guide head 46 of stylet driver 30 and inwardly facing slot 42-1 of guide head 42 of cutting cannula driver 28. As such, outwardly facing rack gear 38-3 of cutting cannula driver 28 and outwardly facing rack gear 44-3 of stylet driver 30 are arranged to be parallel to each other and face in opposite directions away from longitudinal axis 34. Stated differently, each of outwardly facing rack gear 38-3 of cutting cannula driver 28 and outwardly facing rack gear 44-3 of stylet driver 30 are oriented to be parallel to longitudinal axis 34 and on opposite sides of longitudinal axis 34.

Figure 9:
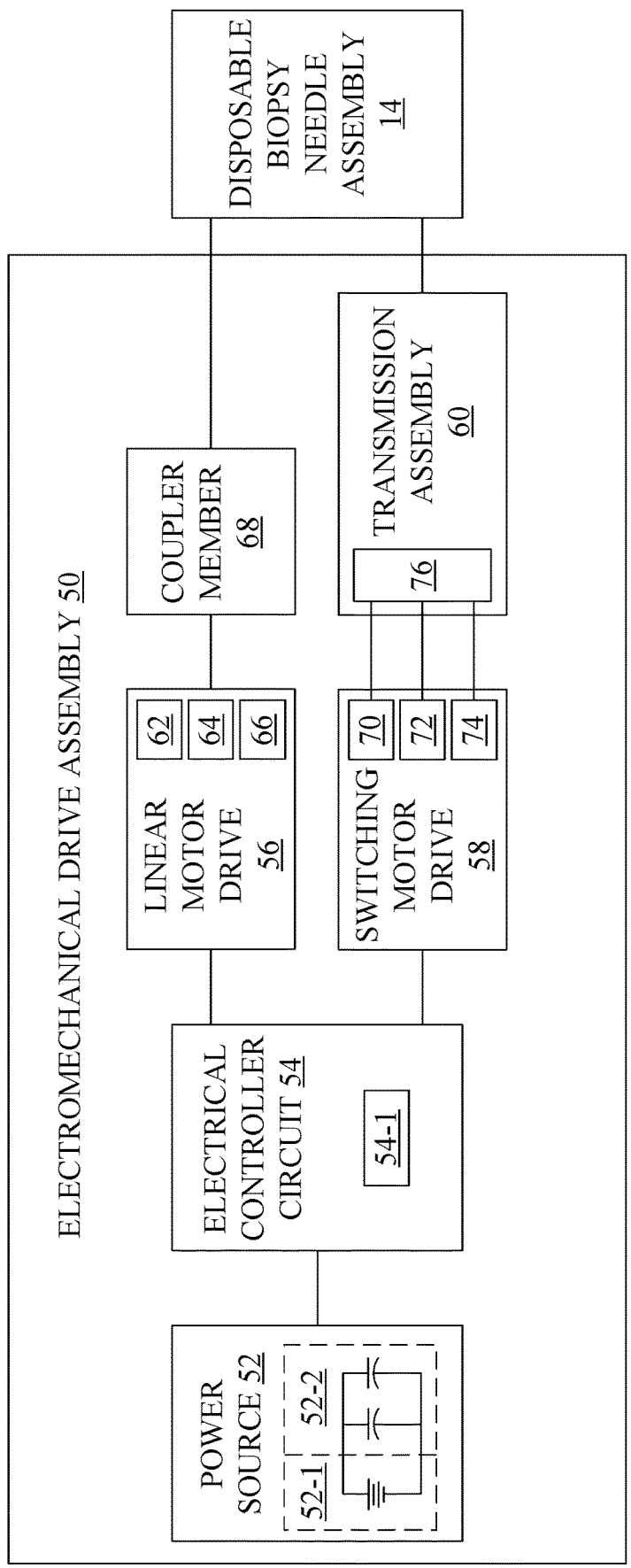
FIG. 9 is a block diagram of the electromechanical drive assembly of the driver assembly of the biopsy device of FIGS. 1 and 2.

Referring to the block diagram of FIG. 9, driver assembly 12 includes an electromechanical drive assembly 50. Electromechanical drive assembly 50 has a power source 52, an electrical controller circuit 54, a linear motor drive 56, a switching motor drive 58, and a transmission assembly 60.

Power source 52 is configured to supply electrical power to each of electrical controller circuit 54, linear motor drive 56, and switching motor drive 58. Power source 52 includes a rechargeable battery 52-1 electrically coupled to a capacitor storage bank 52-2. The capacitor storage bank 52-2 is utilized to provide an increase of available power to linear motor drive 56 during a rapid extension of at least one of the cutting cannula 24 and the stylet 26. Rechargeable battery 52-1 is provided to recharge capacitor storage bank 52-2, as well as to provide non-burst electrical power to electrical controller circuit 54, linear motor drive 56, and switching motor drive 58. Driver assembly 12 may be configured to be received into a charging cradle, or configured to receive a charging cable, to effect a recharging of rechargeable battery 52-1.

Electrical controller circuit 54 is configured to execute program instructions to selectively operate linear motor drive 56 and switching motor drive 58. Also, electrical controller circuit 54 is configured to execute program instructions to activate vacuum source 36 (see FIG. 3), such as for example, when sample notch 26-5 of stylet 26 is exposed so as to draw surrounding tissue into sample notch 26-5, when it is desired to transport a severed tissue sample through stylet 26, or continuously as the cutting cannula 24 is being moved.

Electrical controller circuit 54 includes a microcontroller 54-1. Microcontroller 54-1 includes a microprocessor, on-board non-transitory electronic memory, and component interface circuitry, as is known in the art. Microcontroller 54-1 is configured to receive the user output signals from user interface circuit 12-1 (see FIG. 1), and also to execute program instructions to generate motor control signals to selectively operate linear motor drive 56 and switching motor drive 58, so as to control the extension and retraction of cutting cannula 24 and stylet 26 of disposable biopsy needle assembly 14.

Figure 10:
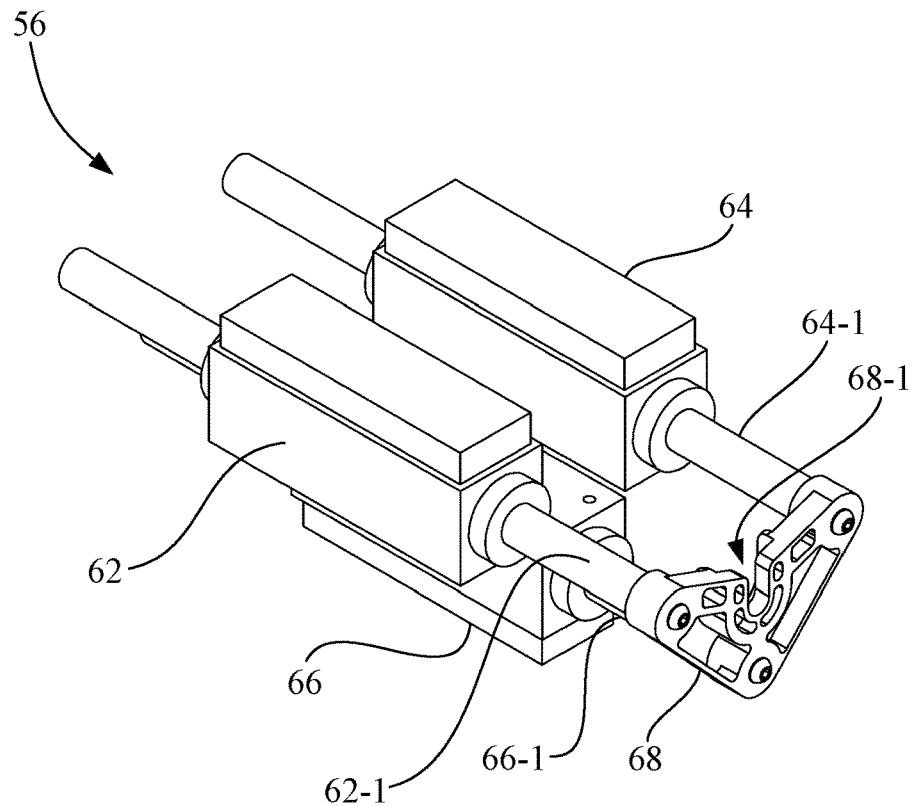
FIG. 10 is a perspective view of a linear motor drive of the electromechanical drive assembly of FIG. 9, attached to a coupler member.
Figure 11:
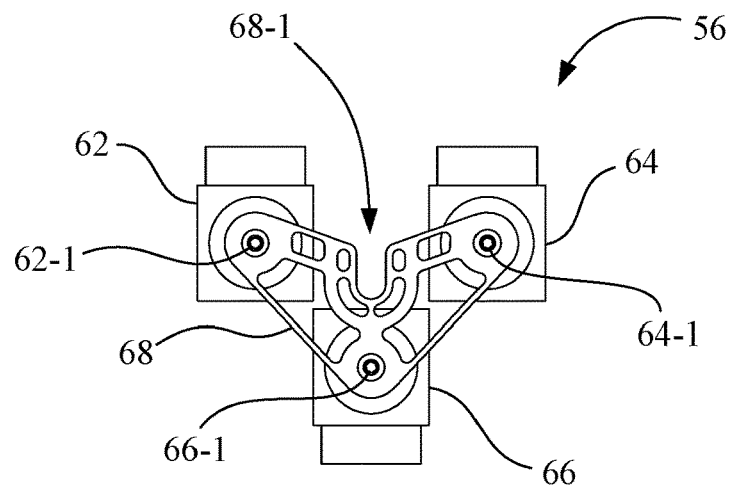
FIG. 11 is an end view of the linear motor drive of FIG. 10, viewed in a direction toward the coupler member.

Referring also to FIGS. 10 and 11, linear motor drive 56 will have at least one linear motor, and in the present embodiment will have three core linear motors that may be operated simultaneously, with the three core linear motors individually identified as linear motor 62, linear motor 64 and linear motor 66. Each of linear motor 62, linear motor 64 and linear motor 66 has an internal coil, and has a respective linearly movable shaft 62-1, shaft 64-1, and shaft 66-1. In the present embodiment, linear motor 62, linear motor 64 and linear motor 66 are arranged in a V-pattern. Also, it is contemplated that linear motor drive 56 may be a single motor with the three motor coils positioned and overmolded.

A coupler member 68 is connected to linear motor drive 56, and may be considered to be an integral part of linear motor drive 56 of electromechanical drive assembly 50. Coupler member 68 is configured to engage the flange 40 of cutting cannula driver 28 of disposable biopsy needle assembly 14 (see also FIGS. 2-4). In particular, a distal end of each of shaft 62-1, shaft 64-1 and shaft 66-1 is connected to a face of coupler member 68. Coupler member 68 is configured as a yoke having an upwardly facing U-shaped slot 68-1 for receiving and drivably engaging flange 40 of cutting cannula driver 28 of disposable biopsy needle assembly 14, and with coupler member 68 being received in drive slot 40-1 of flange 40.

Each of linear motor 62, linear motor 64 and linear motor 66 has integrated positioning, and the location and movement of the respective shafts 62-1, 64-1 and 66-1 may be completely controlled by microcontroller 54-1 of electrical controller circuit 54. Also, the linear motors 62, 64, 66 can provide a constant force, if desired, throughout the travel of coupler member 68 during tissue sampling with disposable biopsy needle assembly 14, e.g., approximately 15 pounds of force. Typically, on prior biopsy devices that use spring propulsion, the spring's highest force is approximately 12 pounds and the spring's lowest preloaded force is approximately two to four pounds.

As an alternative implementation, it is contemplated that one of the linear motors, e.g., linear motor 66, may be disconnected from coupler member 68 and used exclusively to balance the firing force of the other two linear motors. In other words, the force-balancing linear motor 66 will move in the exact opposite direction of the other two linear motors 62, 64, with some applied weight to the shaft of linear motor 66 in order to bring the overall biopsy device momentum to near zero. This would reduce, or eliminate, any jolting force the user might experience during use. As a still further alternative, it is contemplated that an extra linear motor may be used to drive an equivalent weight in the opposite direction of the firing linear motors 62, 64, 66, so as to make the biopsy device a zero-sum momentum device. As such, there would be no jolting of the biopsy device like that which a user may experience in a spring-driven biopsy device when firing.

Figure 12:
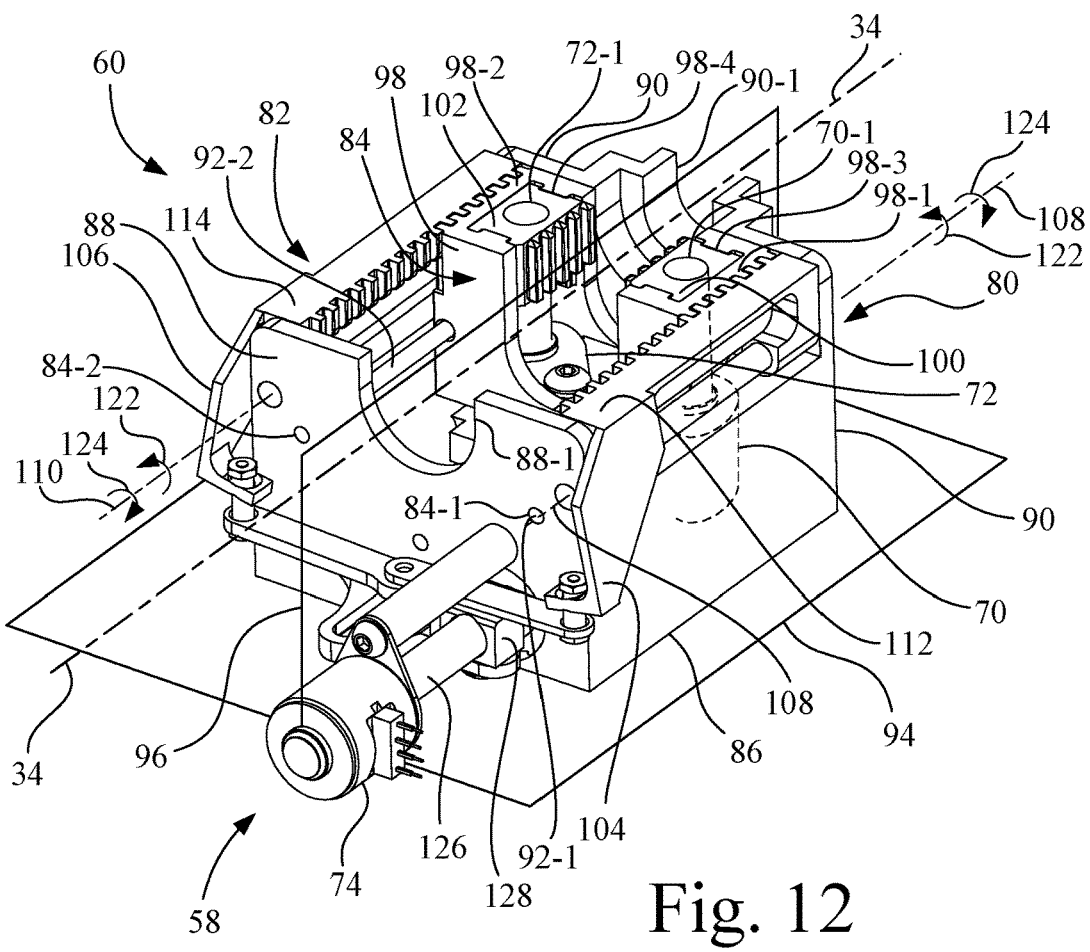
FIG. 12 is a perspective view of the transmission assembly of the electromechanical drive assembly of FIG. 9, with the first and second wing gear plates engaged with the rack carriage.
Figure 13:
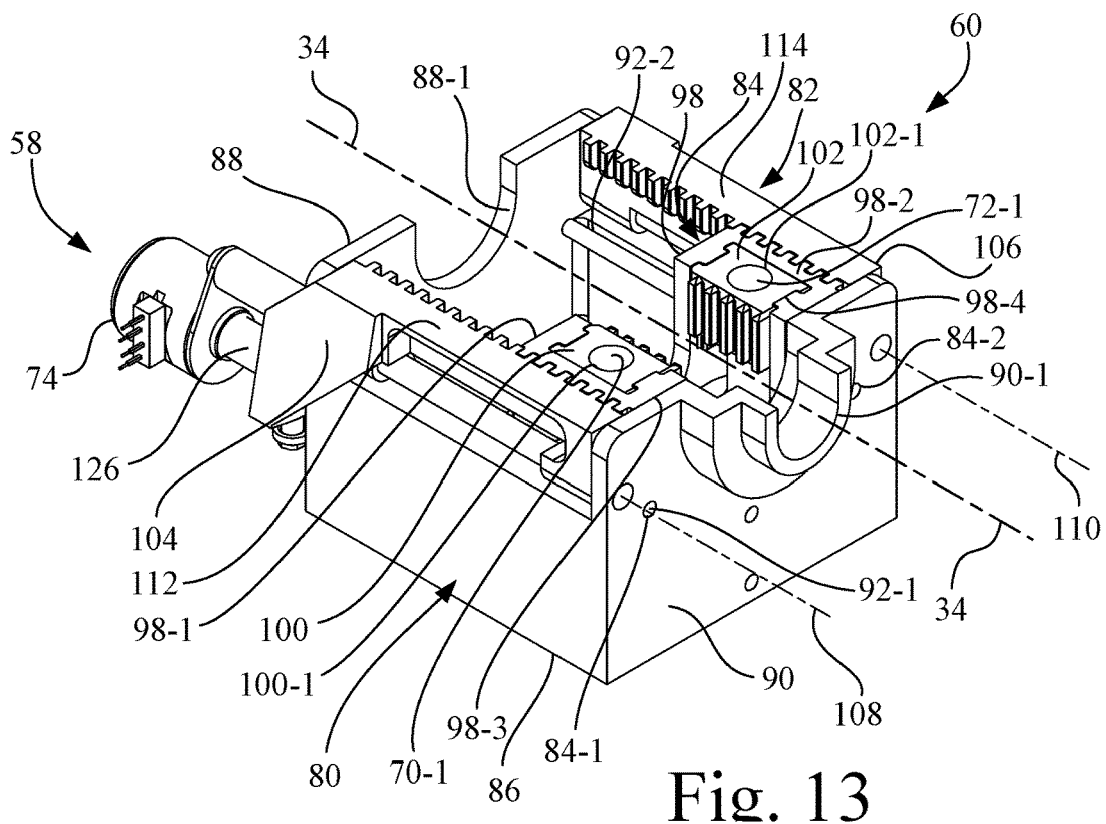
FIG. 13 is another perspective view of the transmission assembly of the electromechanical drive assembly of FIG. 9, with the first and second wing gear plates engaged with the rack carriage.
Figure 14:
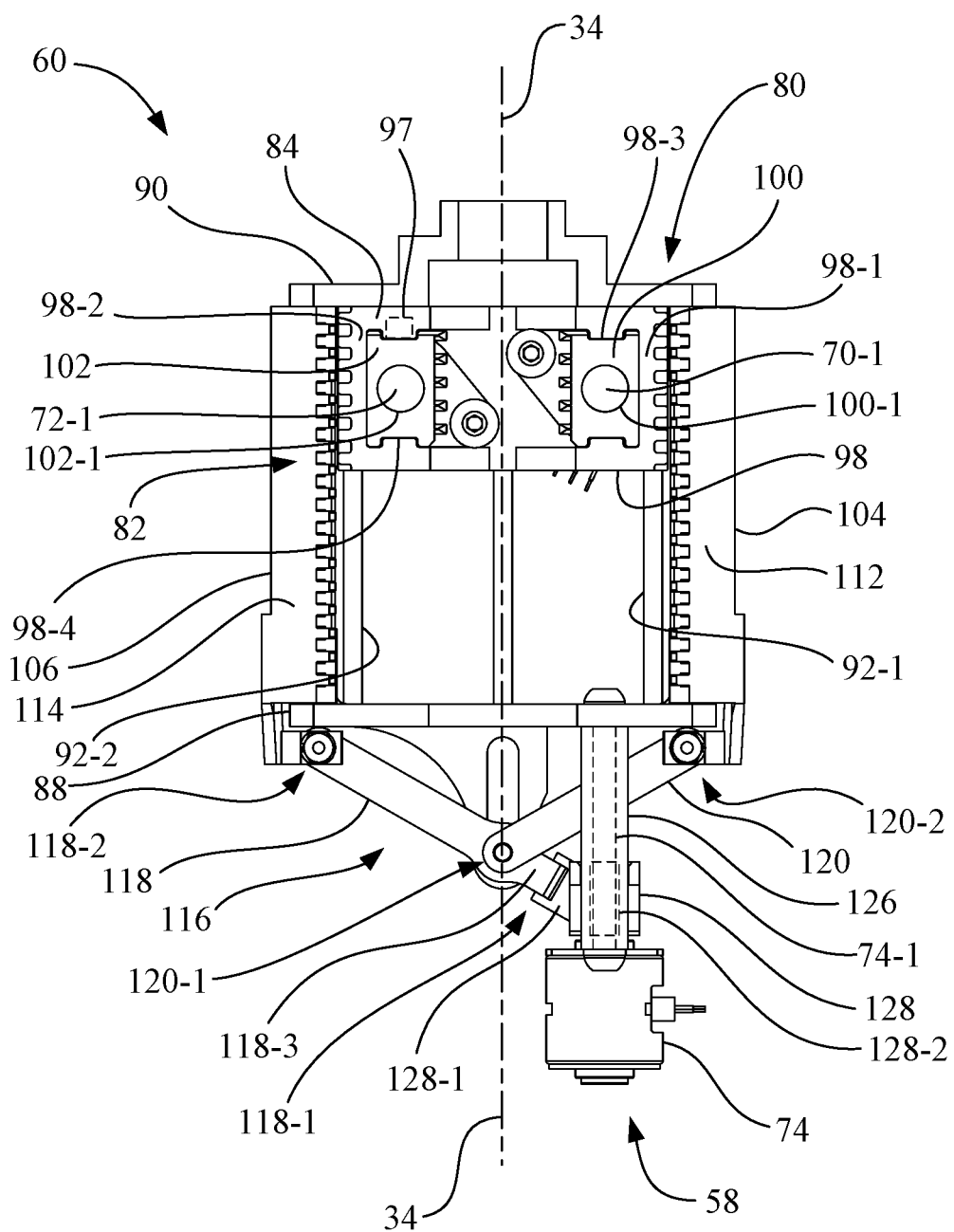
FIG. 14 is a top view of the transmission assembly of the electromechanical drive assembly of FIGS. 12 and 13, with the first and second wing gear plates disengaged from the rack carriage.

FIGS. 12-14 show an assembly that includes switching motor drive 58 and transmission assembly 60. Switching motor drive 58 will have at least one direct current (DC) motor, e.g., a linear motor or a rotary motor, wherein the rotary motor may be a stepper motor or a DC rotary motor. In the present embodiment, switching motor drive 58 will include three direct current (DC) motors, individually identified as motor 70, motor 72, and motor 74. More particularly, in the present embodiment, each of motor 70, motor 72, and motor 74 is a rotary motor, and more preferably, is a stepper motor.

Transmission assembly 60 includes a frame 80, a gear assembly 82, and a rack carriage 84. Gear assembly 82 is mounted to frame 80. Rack carriage 84 is slidably coupled to frame 80. Switching motor drive 58 is drivably coupled to gear assembly 82. Longitudinal axis 34 extends longitudinally through transmission assembly 60.

Frame 80 is mounted to, and is stationary relative to, housing 16 of driver assembly 12 (see FIG. 2). Frame 80 includes a base 86, a proximal wall 88 and a distal wall 90. A pair of guide rods 92-1, 92-2 (see FIGS. 12 and 13) extend from proximal wall 88 to distal wall 90, with each of the pair of guide rods 92-1, 92-2 being arranged to be parallel to longitudinal axis 34. Referring to FIG. 12, base 86 of frame 80 defines a base (e.g., horizontal) plane 94 and a longitudinal plane 96 that extends orthogonally upward from base plane 94 to intersect longitudinal axis 34, i.e., with a longitudinal extent of longitudinal axis 34 lying in the longitudinal plane 96. Proximal wall 88 includes an upwardly facing U-shaped opening 88-1 that serves as a clearance passage for reception of a portion of disposable biopsy needle assembly 14. Distal wall 90 includes an upwardly facing U-shaped cradle 90-1 sized and shaped to receive front alignment bushing 14-1 of disposable biopsy needle assembly 14 (see also FIGS. 2-4).

Rack carriage 84 is slidably coupled to the pair of guide rods 92-1, 92-2, such as by having two pairs of elongate holes 84-1, 84-2 for respectively receiving the pair of guide rods 92-1, 92-2. Rack carriage 84 is linearly movable for linear translation along longitudinal axis 34, relative to frame 80, via a selective coupling provided by gear assembly 82 and one or both of first rack member 38 of cutting cannula driver 28 and second rack member 44 of stylet driver 30 (see FIGS. 3-8). A spring 97 (see FIG. 14) is coupled between the frame 80 and the rack carriage 84, so as to bias rack carriage 84 in a direction toward a distal end of frame 80, i.e., toward distal wall 90 of frame 80.

Rack carriage 84 has a body 98 having a first exterior rack gear 98-1 and a second exterior rack gear 98-2. Each of first exterior rack gear 98-1 and second exterior rack gear 98-2 is a linear gear having a row of teeth that extends parallel to longitudinal axis 34. First exterior rack gear 98-1 and second exterior rack gear 98-2 are located on opposite sides of longitudinal plane 96. Body 98 of rack carriage 84 also has a first vertical slot 98-3 and a second vertical slot 98-4. First vertical slot 98-3 and second vertical slot 98-4 are located in an interior of rack carriage 84, and are located on opposite sides of and facing the longitudinal plane 96. Also, an orthogonal (i.e., vertical) extent of each of first vertical slot 98-3 and second vertical slot 98-4 relative to base plane 94 is parallel to longitudinal plane 96.

Gear assembly 82 includes a first vertical rack gear 100 and a second vertical rack gear 102. First vertical rack gear 100 is slidably received in first vertical slot 98-3 of rack carriage 84. Second vertical rack gear 102 is slidably received in second vertical slot 98-4 of rack carriage 84. Each of first vertical rack gear 100 and second vertical rack gear 102 is a gearing component, and is configured as a linear gear (rack gear) having a row of teeth that faces, and extends parallel to, longitudinal axis 34, i.e., has rack teeth that are spaced apart in a direction parallel to the longitudinal axis 34.

First vertical rack gear 100 and a second vertical rack gear 102 are configured such that first vertical rack gear 100 may releasably engage first rack member 38 of the cutting cannula driver 28, and second vertical rack gear 102 may releasably engage second rack member 44 of the stylet driver 30 (see also FIGS. 2-8).

First vertical rack gear 100 has a threaded hole 100-1 having an internal thread that receives a respective driving portion of switching motor drive 58 to facilitate linear translation of first vertical rack gear 100 in first vertical slot 98-3 of rack carriage 84. Likewise, second vertical rack gear 102 has a threaded hole 102-1 having an internal thread to receive a respective driving portion of switching motor drive 58 to facilitate linear translation of second vertical rack gear 102 in second vertical slot 98-4 of rack carriage 84.

More particularly, motor 70 of switching motor drive 58 has a rotatable shaft 70-1 in the form of a worm gear that is threadably engaged with threaded hole 100-1 of first vertical rack gear 100 to selectively linearly translate first vertical rack gear 100 in first vertical slot 98-3 of rack carriage 84. Accordingly, with activation of motor 70, first vertical rack gear 100 moves linearly in first vertical slot 98-3 of rack carriage 84, up or down. In the orientation of components as shown, an upward linear movement of first vertical rack gear 100 will cause first vertical rack gear 100 to engage first rack member 38 of cutting cannula driver 28, and a downward linear movement of first vertical rack gear 100 will cause first vertical rack gear 100 to disengage from first rack member 38 of cutting cannula driver 28.

Similarly, motor 72 of switching motor drive 58 has a rotatable shaft 72-1 in the form of a worm gear that is threadably engaged with threaded hole 102-1 of second vertical rack gear 102 to selectively linearly translate second vertical rack gear 102 in second vertical slot 98-4 of rack carriage 84, up or down. Accordingly, with activation of motor 72, second vertical rack gear 102 moves linearly in second vertical slot 98-4 of rack carriage 84. In the orientation of components as shown, an upward linear movement of second vertical rack gear 102 will cause second vertical rack gear 102 to engage second rack member 44 of stylet driver 30, and a downward linear movement of second vertical rack gear 102 will cause second vertical rack gear 102 to disengage from second rack member 44 of stylet driver 30.

Gear assembly 82 of transmission assembly 60 further includes a first wing gear plate 104 and a second wing gear plate 106. First wing gear plate 104 and second wing gear plate 106 are configured to perform selective internal locking functions for transmission assembly 60, i.e., to selectively lock or unlock rack carriage 84, so as to selectively prohibit or allow (facilitate) movement of rack carriage 84 along longitudinal axis 34. First wing gear plate 104 is pivotably coupled to the frame 80 at a first pivot axis 108 and second wing gear plate 106 is pivotably coupled to the frame 80 at a second pivot axis 110. First pivot axis 108 and second pivot axis 110 are on opposite sides of longitudinal plane 96. The pivotable coupling may be made, for example, with a pin-hole, or hinge, arrangement.

First wing gear plate 104 has a first linear gear 112 that is positionable to selectively engage first exterior rack gear 98-1 of the rack carriage 84. First linear gear 112, i.e., a rack gear, has a row of teeth that extends parallel to longitudinal axis 34, i.e., has rack teeth that are spaced apart in a direction parallel to the longitudinal axis 34. Likewise, second wing gear plate 106 has a second linear gear 114 that is positionable to selectively engage second exterior rack gear 98-2 of the rack carriage 84. Second linear gear 114, i.e., a rack gear, has a row of teeth that extends parallel to longitudinal axis 34, i.e., has rack teeth that are spaced apart in a direction parallel to the longitudinal axis 34. First linear gear 112 and second linear gear 114 may be simultaneously operated to respectively engage first exterior rack gear 98-1 and second exterior rack gear 98-2, as shown in FIGS. 12 and 13, so as to lock a longitudinal position of the rack carriage 84 to prevent movement of the rack carriage 84 along the longitudinal axis 34; however, when disengaged, rack carriage 84 may be moved to a new longitudinal position along longitudinal axis 34.

A pivot linkage 116 (see FIG. 14) is connected to each of first wing gear plate 104 and second wing gear plate 106.

Pivot linkage 116 is configured to simultaneously pivot first wing gear plate 104 in a first rotational direction 122 (e.g., counterclockwise in FIG. 12) around first pivot axis 108 and pivot second wing gear plate 106 in a second rotational direction 124 (e.g., clockwise in FIG. 12) around second pivot axis 110, so as to simultaneously engage first linear gear 112 with first exterior rack gear 98-1 of rack carriage 84 and engage second linear gear 114 with second exterior rack gear 98-2 of rack carriage 84, so as to lock a longitudinal position of rack carriage 84 to prevent movement of rack carriage 84 along longitudinal axis 34. First rotational direction 122 is opposite to second rotational direction 124.

Referring to FIGS. 12 and 14, pivot linkage 116 is configured to simultaneously pivot first wing gear plate 104 in second rotational direction 124 around the first pivot axis 108 and pivot second wing gear plate 106 in first rotational direction 122 around the second pivot axis 110, so as to simultaneously disengage first linear gear 112 from first exterior rack gear 98-1 of the rack carriage 84 and disengage second linear gear 114 from second exterior rack gear 98-2 of rack carriage 84, so as to facilitate movement of rack carriage 84 along longitudinal axis 34.

In particular, pivot linkage 116 includes an elongate member 118 and an elongate member 120. Elongate member 118 has a proximal end 118-1, a distal end 118-2, and a free end arm 118-3 that is distal to proximal end 118-1. Elongate member 120 has a proximal end 120-1 and a distal end 120-2. Distal end 118-2 of elongate member 118 is pivotably coupled to second wing gear plate 106. Distal end 120-2 of elongate member 120 is pivotably coupled to first wing gear plate 104. Proximal end 120-1 of elongate member 120 is pivotably coupled to elongate member 118 at a location between proximal end 118-1 and a distal end 118-2, and in turn defines a length of free end arm 118-3. Free end arm 118-3 of pivot linkage 116 is drivably coupled to motor 74 of switching motor drive 58.

In relation to motor 74, switching motor drive 58 includes an elongate rail 126 that is interposed between motor 74 and proximal wall 88 of frame 80 of transmission assembly 60, with elongate rail 126 being connected to each of a housing of motor 74 and proximal wall 88 of frame 80. Elongate rail 126 is oriented to be substantially parallel to longitudinal axis 34.

A coupling slider 128 is slidably coupled to elongate rail 126 so as to linearly translate along elongate rail 126. Coupling slider 128 further includes a pivoting drive slide channel 128-1 to slidably receive at least a portion of free end arm 118-3 of elongate member 118 of pivot linkage 116. Coupling slider 128 further includes a threaded hole 128-2 having an internal thread that receives a respective driving portion of motor 74.

More particularly, motor 74 of switching motor drive 58 has a rotatable shaft 74-1 in the form of a worm gear that is threadably engaged with threaded hole 128-2 of coupling slider 128, such that a rotation of rotatable shaft 74-1 of motor 74 results in a linear translation of coupling slider 128, which in turn operates pivot linkage 116 to in turn simultaneously pivot first wing gear plate 104 around the first pivot axis 108 and pivot second wing gear plate 106 around the second pivot axis 110.

Thus, for example, rotating rotatable shaft 74-1 of motor 74 in one direction slides coupling slider 128 in a direction toward proximal wall 88 of frame 80 of transmission assembly 60, as depicted in FIGS. 12 and 13, thereby simultaneously pivoting first wing gear plate 104 in first rotational direction 122 (e.g., counterclockwise in FIG. 12) and pivot second wing gear plate 106 in a second rotational direction 124 (e.g., clockwise in FIG. 12) so as to simultaneously engage first linear gear 112 with first exterior rack gear 98-1 of rack carriage 84 and engage second linear gear 114 with second exterior rack gear 98-2 of rack carriage 84, respectively.

Conversely, rotating rotatable shaft 74-1 of motor 74 in the opposite direction slides coupling slider 128 in a direction away from proximal wall 88 of frame 80 of transmission assembly 60, as depicted in FIG. 14, thereby simultaneously pivoting first wing gear plate 104 in second rotational direction 124 (e.g., clockwise in FIG. 12) and pivoting second wing gear plate 106 in first rotational direction 122

(e.g., counterclockwise in FIG. 12) so as to simultaneously disengage first linear gear 112 from first exterior rack gear 98-1 of rack carriage 84 and disengage second linear gear 114 from second exterior rack gear 98-2 of rack carriage 84, respectively.

In accordance with the above, electrical controller circuit 54 is configured to execute program instructions to activate switching motor drive 58 to cause gear assembly 82 to selectively engage one or both of first rack member 38 of cutting cannula driver 28 and second rack member 44 of the stylet driver 30, and is configured to execute program instructions to activate linear motor drive 56 to move the coupler member 68 along the longitudinal axis 34, so as to obtain a tissue sample.

Figure 15:
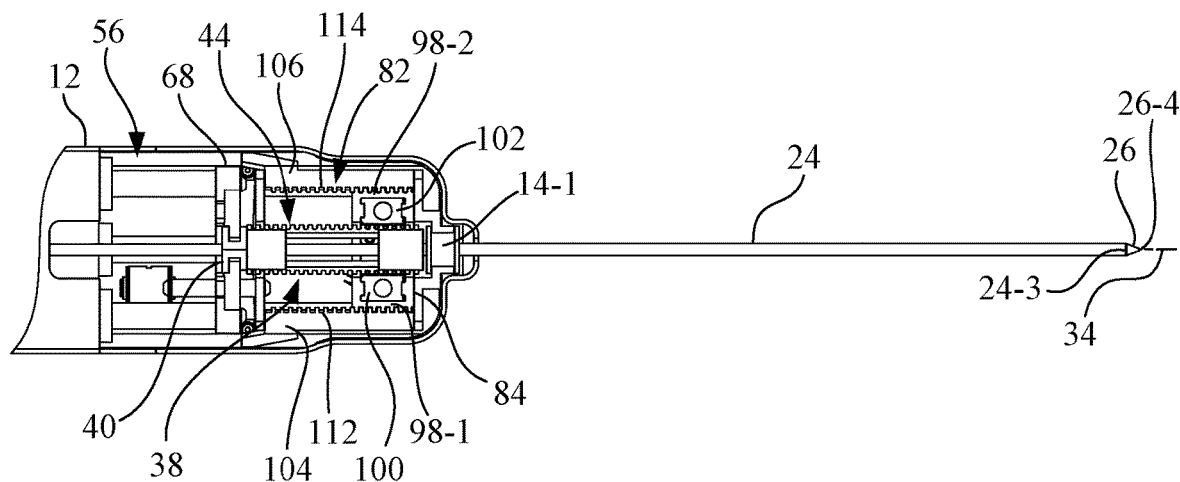
FIG. 15 is an enlarged top view of a distal portion of the driver assembly of the biopsy device of FIG. 2, showing components of the electromechanical drive assembly of the driver assembly and the disposable biopsy needle assembly in the home position.

FIG. 15 shows electromechanical drive assembly 50 with its various components in a home position.

Figure 16:
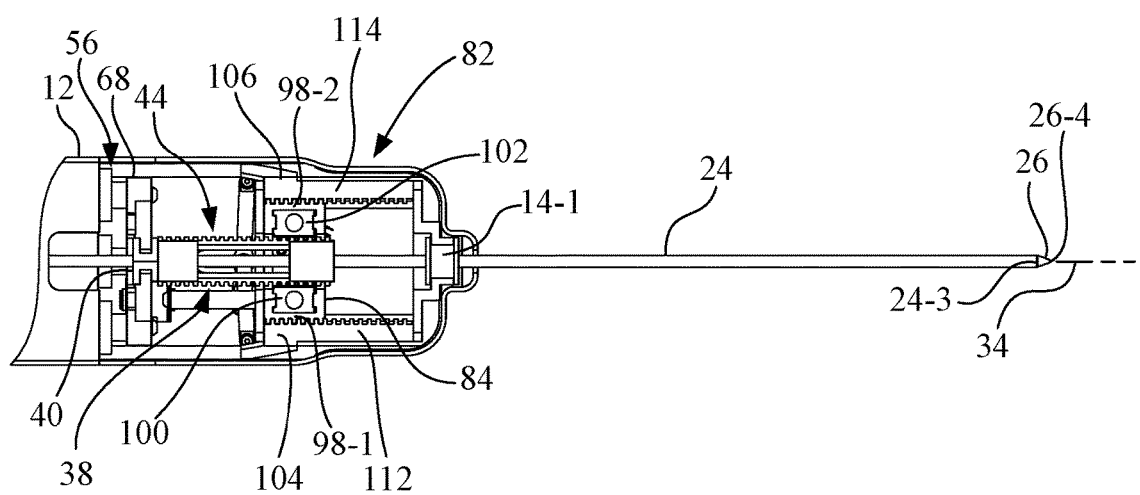
FIG. 16 is an enlarged top view of a distal portion of the driver assembly of the biopsy device of FIG. 2, showing components of the electromechanical drive assembly of the driver assembly and the disposable biopsy needle assembly in the prime (retracted) position.

Referring to FIG. 16 in relation to FIGS. 2-14, cutting cannula 24 and the stylet 26 are moved to a primed position, i.e., a fully retracted position. Component movement to the primed position may be initiated, for example, by depressing prime-pierce button 12-2 (see FIG. 1) a first time, wherein user interface circuit 12-1 sends a corresponding user output signal to electrical controller circuit 54. In particular, to move from the home position of FIG. 15, electrical controller circuit 54 executes program instructions to retract first wing gear plate 104 and second wing gear plate 106 (see also FIG. 14), such that simultaneously, first linear gear 112 disengages first exterior rack gear 98-1 of rack carriage 84 and second linear gear 114 disengages second exterior rack gear 98-2 of rack carriage 84, so as to unlock rack carriage 84 and permit a linear translation of rack carriage 84 along longitudinal axis 34. Electrical controller circuit 54 then executes program instructions to activate switching motor drive 58 to cause first vertical rack gear 100 and second vertical rack gear 102 of gear assembly 82 to engage both of first rack member 38 of cutting cannula driver 28 and second rack member 44 of stylet driver 30, respectively. After gear assembly 82 is engaged with both of first rack member 38 and second rack member 44, electrical controller circuit 54 then executes program instructions to activate linear motor drive 56 to move coupler member 68 in a proximal direction to retract both of cutting cannula 24 and stylet 26 to the primed position depicted in FIG. 16. Electrical controller circuit 54 may then execute program instructions to collapse first wing gear plate 104 and second wing gear plate 106, such that, simultaneously, first linear gear 112 engages first exterior rack gear 98-1 of rack carriage 84 and second linear gear 114 engages second exterior rack gear 98-2 of rack carriage 84 (see, e.g., FIGS. 12 and 13), so as to lock the longitudinal position of rack carriage 84 in the retracted position and prevent movement of rack carriage 84 along longitudinal axis 34. It is noted that the only time that first wing gear plate 104 and second wing gear plate 106 are retracted, i.e., disengaged from rack carriage 84, is when it is desired to reposition rack carriage 84.

Figure 17:
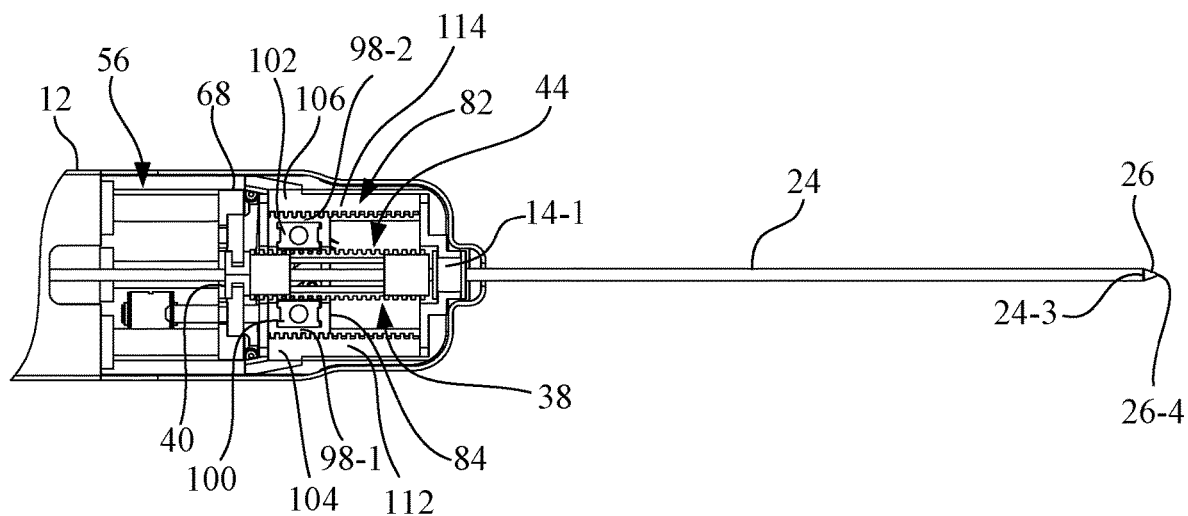
FIG. 17 is an enlarged top view of a distal portion of the driver assembly of the biopsy device of FIG. 2, showing components of the electromechanical drive assembly of the driver assembly and the disposable biopsy needle assembly in the pierce (extended) position.

Referring to FIG. 17 in relation to FIGS. 2-14, cutting cannula 24 and the stylet 26 are moved from the primed position (depicted in FIG. 16) to a piercing position, i.e., a fully extended position. Component movement to the piercing position may be initiated, for example, by depressing prime-pierce button 12-2 (see FIG. 1) a second time, wherein user interface circuit 12-1 sends a corresponding user output signal to electrical controller circuit 54. In particular, electrical controller circuit 54 executes program instructions to activate switching motor drive 58 to cause first vertical rack gear 100 and second vertical rack gear 102 of gear assembly 82 to disengage from both of first rack member 38 of cutting cannula driver 28 and second rack member 44 of the stylet driver 30, and then executes program instructions to activate linear motor drive 56 to rapidly move coupler member 68 in a distal direction so as to rapidly distally extend (i.e., fire) both of cutting cannula 24 and stylet 26 to the pierce position, depicted in FIG. 17.

Figure 18:
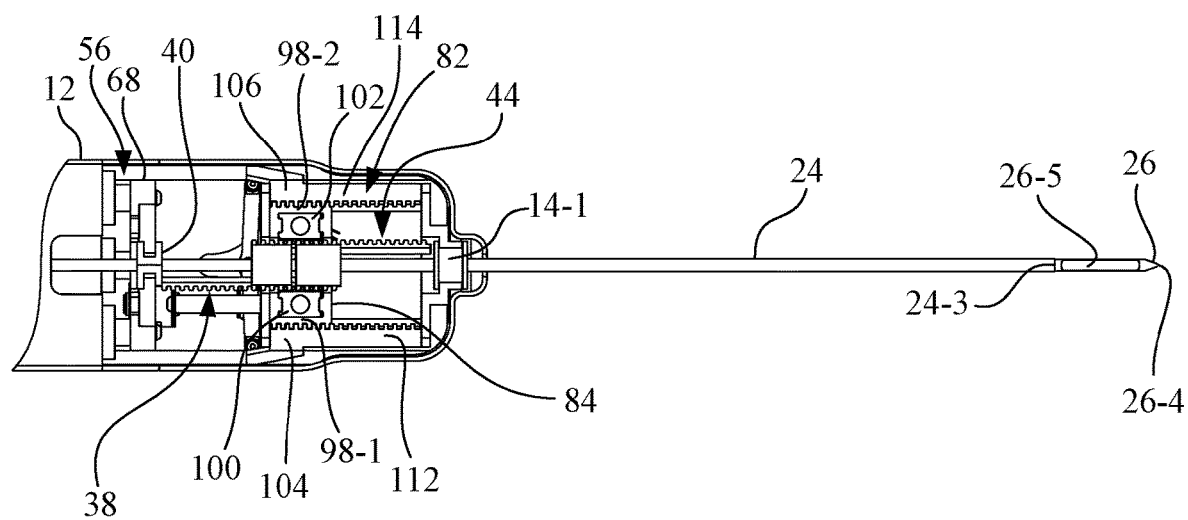
FIG. 18 is an enlarged top view of a distal portion of the driver assembly of the biopsy device of FIG. 2, showing components of the electromechanical drive assembly of the driver assembly and the disposable biopsy needle assembly in the sample notch open position, wherein the cutting cannula is retracted relative to the stylet to expose the sample notch of the stylet.

Referring to FIG. 18 in relation to FIGS. 2-14, cutting cannula 24 is moved from the pierce position (depicted in FIG. 17) to a sample notch open position, i.e., cutting cannula 24 is partially retracted to expose all, or a predetermined portion of, sample notch 26-5 of stylet 26. Component movement to the sample notch open position may be initiated, for example, by depressing sample button 12-3 (see FIG. 1) a first time, wherein user interface circuit 12-1 sends a corresponding user output signal to electrical controller circuit 54. In particular, electrical controller circuit 54 executes program instructions to activate switching motor drive 58 to cause first vertical rack gear 100 of gear assembly 82 to be disengaged from first rack member 38 of the cutting cannula driver 28, and to cause second vertical rack gear 102 of gear assembly 82 to engage with the second rack member 44 of the stylet driver 30 so as to lock the stylet 26 in the pierce position. Electrical controller circuit 54 then executes program instructions to activate linear motor drive 56 to move the coupler member 68 in a proximal direction to retract cutting cannula 24 relative to the stylet 26 to expose sample notch 26-5 in the stylet 26 by a predetermined amount. The predetermined amount may be selected by the user prior to beginning the biopsy procedure, so as to select a desired size of the tissue sample to be taken. Electrical controller circuit 54 may also execute program instructions to activate vacuum source 36 (see FIG. 3) as the cutting cannula 24 is being retracted.

Figure 19:
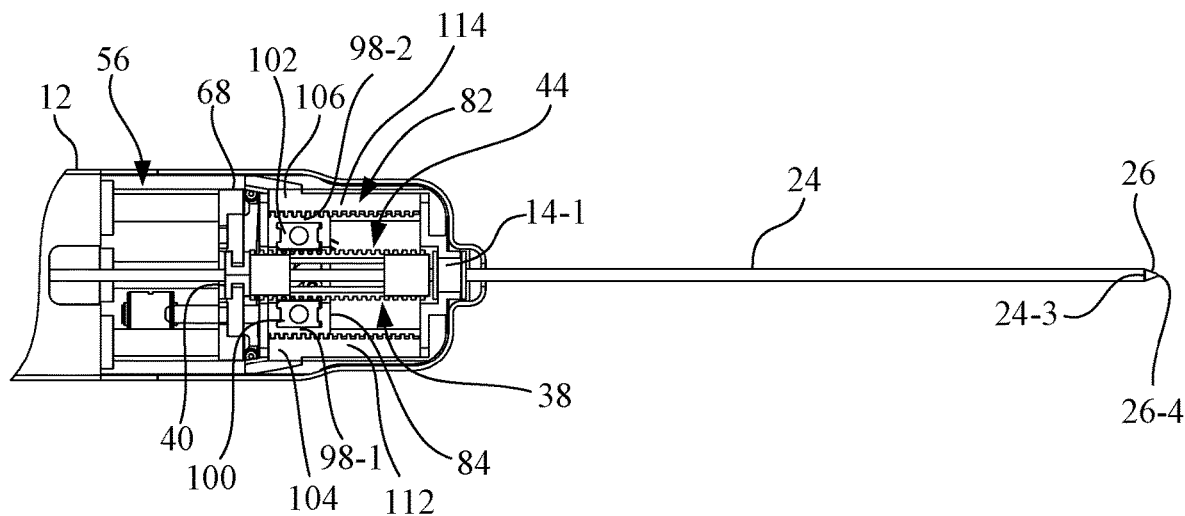
FIG. 19 is an enlarged top view of a distal portion of the driver assembly of the biopsy device of FIG. 2, showing components of the electromechanical drive assembly of the driver assembly and the disposable biopsy needle assembly in the sample acquisition position, wherein the cutting cannula is fired forward to cover the sample notch of the stylet.

Referring to FIG. 19 in relation to FIGS. 2-14, cutting cannula 24 is moved from the sample notch open position (depicted in FIG. 18) to a sample acquisition position, i.e., cutting cannula 24 extends distally beyond sample notch 26-5 of stylet 26, so as to sever tissue drawn into sample notch 26-5. Component movement to the sample acquisition position may be initiated, for example, by depressing sample button 12-3 (see FIG. 1) a second time, wherein user interface circuit 12-1 sends a corresponding user output signal to electrical controller circuit 54. Alternatively, sample acquisition may occur automatically following the positioning of the components in the sample notch open position.

In particular, with first vertical rack gear 100 of gear assembly 82 disengaged from the first rack member 38 of cutting cannula driver 28 and second vertical rack gear 102 of gear assembly 82 engaged with the second rack member 44 of the stylet driver 30, electrical controller circuit 54 executes program instructions to activate linear motor drive 56 to move the coupler member 68 in a distal direction to rapidly distally extend (i.e., fire) cutting cannula 24 relative to stylet 26 to cover sample notch 26-5 in stylet 26, so as to sever a tissue sample from surrounding tissue. Electrical controller circuit 54 may also execute program instructions to activate vacuum source 36 (see FIG. 3) to transport the severed tissue sample to sample receptacle 32.

Figure 20:
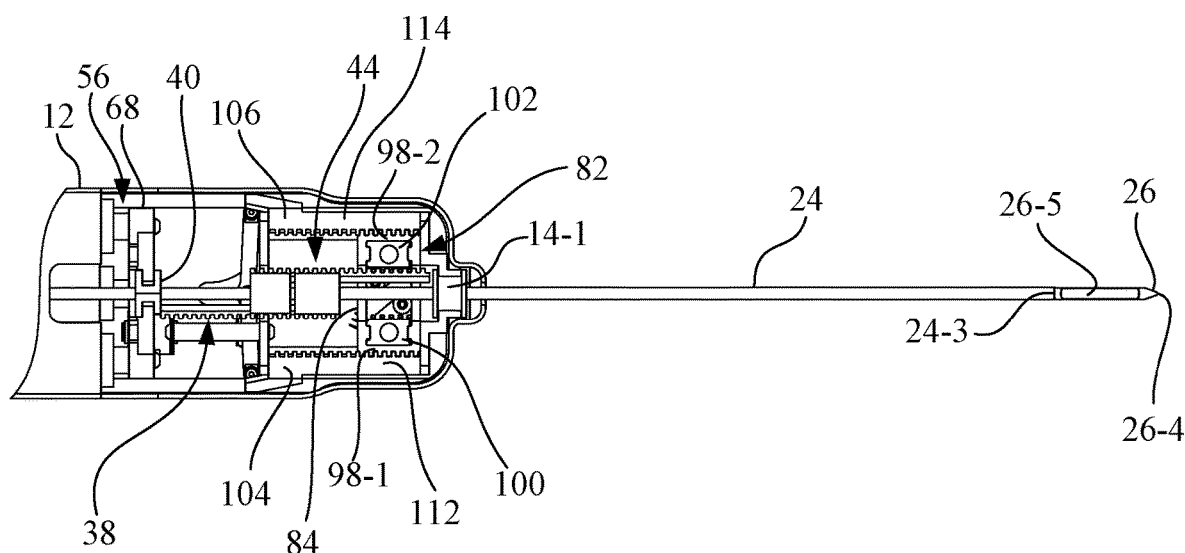
FIG. 20 is an enlarged top view of a distal portion of the driver assembly of the biopsy device of FIG. 2, showing components of the electromechanical drive assembly of the driver assembly and the disposable biopsy needle assembly in an alternative position wherein the prime and pierce operations were bypassed, and wherein the cutting cannula is retracted relative to the stylet to expose the sample notch of the stylet.

Alternatively, from the home position depicted in FIG. 15, it is possible to bypass the prime and pierce operations associated with FIGS. 16 and 17, and directly execute the sample operation associated with FIGS. 18 and 19. However, in this case, as depicted in FIG. 20, rack carriage 84 may remain in the distal (forward) position.

The following items also relate to the invention:

In one form, the invention relates to a biopsy device comprising a disposable needle assembly having a first cannula, a second cannula, a first cannula driver, and a second cannula driver. The first cannula driver is connected to a first portion of the first cannula. The second cannula driver is connected to a first portion of the second cannula. The first cannula driver has a first rack member and a flange connected to the first rack member. The second cannula driver has a second rack member. A drive assembly has a power source, a linear motor drive having at least one linear motor, a transmission assembly, a switching motor drive having at least one DC motor, and an electrical controller circuit. The power source is configured to supply electrical power to each of the linear motor drive, the switching motor drive, and the electrical controller circuit. The electrical controller circuit is configured to execute program instructions to selectively operate the linear motor drive and the switching motor drive. The transmission assembly has a gear assembly drivably coupled to the switching motor drive. The gear assembly is configured to releasably engage at least one of the first rack member of the first cannula driver and the second rack member of the second cannula driver. A coupler member is connected to the linear motor drive. The coupler member is configured to engage the flange of the first cannula driver.

The electrical controller circuit may be configured to execute program instructions to activate the switching motor drive to cause the gear assembly to selectively engage the first rack member of the first cannula driver and the second rack member of the second cannula driver, and may execute program instructions to activate the linear motor drive to move the coupler member along the longitudinal axis.

The electrical controller circuit may be configured to execute program instructions to activate the switching motor drive to cause the gear assembly to engage both of the first rack member of the first cannula driver and the second rack member of the second cannula driver, and may execute program instructions to activate the linear motor drive to move the coupler member in a proximal direction to retract both of the first cannula and the second cannula to a primed position when the gear assembly is engaged with both of the first rack member and the second rack member.

The electrical controller circuit may be configured to execute program instructions to activate the switching motor drive to cause the gear assembly to disengage from both of the first rack member of the first cannula driver and the second rack member of the second cannula driver, and may execute program instructions to activate the linear motor drive to move the coupler member in a distal direction to extend both of the first cannula and the second cannula to a pierce position.

The electrical controller circuit may be configured to execute program instructions to activate the switching motor drive to cause the gear assembly to be disengaged from the first rack member of the first cannula driver and to cause the gear assembly to engage with the second rack member of the second cannula driver, the gear assembly configured to lock the second cannula in the pierce position, and may execute program instructions to activate the linear motor drive to move the coupler member in a proximal direction to retract the first cannula relative to the second cannula to expose a sample notch in the second cannula.

In any of the preceding embodiments, a vacuum source may be in fluid communication with the sample notch, and the electrical controller circuit may be configured to execute program instructions to activate the vacuum source as the first cannula is being retracted.

In any of the preceding embodiments, with the gear assembly disengaged from the first rack member of the first cannula driver and engaged with the second rack member of the second cannula driver, the electrical controller circuit may execute program instructions to activate the linear motor drive to move the coupler member in a distal direction to move the first cannula relative to the second cannula to cover the sample notch in the second cannula.

In any of the preceding embodiments, a vacuum source may be in fluid communication with a lumen of the second cannula, and the electrical controller circuit may execute program instructions to activate the vacuum source as the first cannula is being moved.

In any of the preceding embodiments, the power source may include a rechargeable battery configured to be electrically coupled to a capacitor storage bank. Optionally, a capacitor storage bank may be configured to provide an increase of available power to the linear motor drive during a rapid extension of at least one of the first cannula and the second cannula.

In any of the preceding embodiments, the drive assembly may have a longitudinal axis that extends longitudinally through the transmission assembly, and wherein the transmission assembly includes a frame and a rack carriage slidably coupled to the frame and configured for linear translation along the longitudinal axis. The frame may have a base defining a horizontal plane and a longitudinal plane that extends orthogonally upward from the horizontal plane, with a longitudinal extent of the longitudinal axis lying in the longitudinal plane.

The rack carriage may have a body having a first exterior rack gear and a second exterior rack gear. The first exterior rack gear and the second exterior rack gear may be located on opposite sides of the longitudinal plane. The body of the rack carriage may have a first vertical slot and a second vertical slot. The first vertical slot and the second vertical slot may be located in an interior of the rack carriage and located on opposite sides of and facing the longitudinal plane. The gear assembly may include a first vertical rack gear slidably received in the first vertical slot and a second vertical rack gear slidably received in the second vertical slot, wherein each of the first vertical rack gear and the second vertical rack gear has rack teeth that are spaced apart in a direction parallel to the longitudinal axis. The switching motor drive may include a first motor coupled to the first vertical rack gear and configured to selectively linearly translate the first vertical rack gear up and down in the first vertical slot of the rack carriage, such that the first vertical rack gear selectively engages the first rack member of the first cannula driver. The switching motor drive may include a second motor coupled to the second vertical rack gear and configured to selectively linearly translate the second vertical rack gear up and down in the second vertical slot of the rack carriage, such that the second vertical rack gear selectively engages the second rack member of the second cannula driver.

The transmission assembly may include a first wing gear plate and a second wing gear plate. The first wing gear plate may be pivotably coupled to the frame at a first pivot axis and the second wing gear plate is pivotably coupled to the frame at a second pivot axis. The first pivot axis and the second pivot axis may be on opposite sides of the longitudinal plane. The first wing gear plate may have a first linear gear and the second wing gear plate may have a second linear gear.

A pivot linkage may be connected to each of the first wing gear plate and the second wing gear plate. The pivot linkage may be configured to engage the first linear gear with the first exterior rack gear of the rack carriage when the first wing gear plate is pivoted by the pivot linkage in a first rotational direction around the first pivot axis and to engage the second linear gear with the second exterior rack gear of the rack carriage when the second wing gear plate is pivoted by the pivot linkage in a second rotational direction around the second pivot axis, wherein the first rotational direction is opposite to the second rotational direction. The pivot linkage may be configured to disengage the first linear gear from the first exterior rack gear of the rack carriage when the first wing gear plate is pivoted by the pivot linkage in the second rotational direction around the first pivot axis and to disengage the second linear gear from the second exterior rack gear of the rack carriage when the second wing gear plate is pivoted by the pivot linkage in the first rotational direction around the second pivot axis. The switching motor drive may include a third motor drivably coupled to the pivot linkage.

In any of the preceding embodiments having first, second, and third motors, each of the first motor, the second motor and the third motor may be a rotary motor.

In any of the preceding embodiments, a spring may be coupled between the frame and the rack carriage, with the spring configured to bias the rack carriage toward a distal end of the frame.

In another form, the invention relates to a biopsy device, comprising a disposable needle assembly having a cutting cannula, a stylet, a cannula driver, and a stylet driver. The cannula driver is connected to a first portion of the cutting cannula. The stylet driver is connected to a first portion of the stylet. The cannula driver has a first rack member and a flange connected to the first rack member. The stylet driver has a second rack member. A linear motor drive has at least one linear motor. A coupler member is connected to the linear motor drive. The coupler member is configured to engage the flange of the cannula driver of the disposable needle assembly. A switching motor drive has at least one rotary motor. A transmission assembly has a gear assembly drivably coupled to the switching motor drive. The gear assembly is configured to releasably engage at least one of the first rack member of the cannula driver and the second rack member of the stylet driver. An electrical controller circuit is configured to execute program instructions to selectively operate the linear motor drive and the switching motor drive.

The drive assembly may have a longitudinal axis that extends longitudinally through the transmission assembly. The transmission assembly may have a frame and a rack carriage slidably coupled to the frame and configured for linear translation along the longitudinal axis. The frame may have a base defining a horizontal plane and a longitudinal plane that extends orthogonally upward from the horizontal plane, with a longitudinal extent of the longitudinal axis lying in the longitudinal plane.

The rack carriage may have a body having a first exterior rack gear and a second exterior rack gear. The first exterior rack gear and the second exterior rack gear may be located on opposite sides of the longitudinal plane. The body of the rack carriage may have a first vertical slot and a second vertical slot, with the first vertical slot and the second vertical slot located in an interior of the rack carriage and located on opposite sides of and facing the longitudinal plane.

The gear assembly may include a first vertical rack gear slidably received in the first vertical slot and a second vertical rack gear slidably received in the second vertical slot, with each of the first vertical rack gear and the second vertical rack gear having rack teeth that are spaced apart in a direction parallel to the longitudinal axis.

The switching motor drive may include a first motor coupled to the first vertical rack gear and configured to selectively linearly translate the first vertical rack gear up and down in the first vertical slot of the rack carriage, such that the first vertical rack gear selectively engages the first rack member of the cannula driver. The switching motor drive may include a second motor coupled to the second vertical rack gear and configured to selectively linearly translate the second vertical rack gear up and down in the second vertical slot of the rack carriage, such that the second vertical rack gear selectively engages the second rack member of the stylet driver.

The transmission assembly may include a first wing gear plate and a second wing gear plate. The first wing gear plate is pivotably coupled to the frame at a first pivot axis and the second wing gear plate is pivotably coupled to the frame at a second pivot axis, the first pivot axis and the second pivot axis being on opposite sides of the longitudinal plane. The first wing gear plate has a first linear gear and the second wing gear plate has a second linear gear.

A pivot linkage may be connected to each of the first wing gear plate and the second wing gear plate. The pivot linkage may be configured to simultaneously pivot the first wing gear plate in a first rotational direction around the first pivot axis and pivot the second wing gear plate in a second rotational direction around the second pivot axis, with the first rotational direction being opposite to the second rotational direction, so as to simultaneously engage the first linear gear with the first exterior rack gear of the rack carriage and engage the second linear gear with the second exterior rack gear of the rack carriage, so as to lock a longitudinal position of the rack carriage to prevent movement of the rack carriage along the longitudinal axis.

The pivot linkage may be configured to simultaneously pivot the first wing gear plate in the second rotational direction around the first pivot axis and pivot the second wing gear plate in the first rotational direction around the second pivot axis, so as to simultaneously disengage the first linear gear from the first exterior rack gear of the rack carriage and disengage the second linear gear from the second exterior rack gear of the rack carriage, so as to facilitate movement of the rack carriage along the longitudinal axis.

The switching motor drive may include a third motor drivably coupled to the pivot linkage.

In any of the preceding embodiments having first, second, and third motors, each of the first motor, the second motor and the third motor may be a rotary motor.

In any of the preceding embodiments, a spring may be coupled between the frame and the rack carriage, the spring being configured to bias the rack carriage toward a distal end of the frame.

As used herein, including the claims, the terms "horizontal" and "vertical" are used for convenience to define an orthogonal relationship in space, without necessarily corresponding to earth horizontal and vertical. Also, the terms "up" and "down" define opposite directions in space in a vertical orientation. As used herein, the terms "parallel" and "orthogonal" are intended to include slight variations associated with normal manufacturing tolerances, and unless otherwise stated, include a variation of plus or minus 0.5 degrees. The term "substantially parallel" means a range of parallel, plus or minus five degrees. The term "approximately" means the base value, plus or minus three percent.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy device, comprising:
    a disposable needle assembly having a first cannula, a second cannula, a first cannula driver, and a second cannula driver, the first cannula driver connected to a first portion of the first cannula, the second cannula driver being connected to a first portion of the second cannula, the first cannula driver having a first rack member and a flange connected to the first rack member, the second cannula driver having a second rack member; and
    a drive assembly having a power source, a linear motor drive having at least one linear motor, a transmission assembly, a switching motor drive having at least one DC motor, and an electrical controller circuit, the power source configured to supply electrical power to each of the linear motor drive, the switching motor drive, and the electrical controller circuit;
    the electrical controller circuit configured to execute program instructions to selectively operate the linear motor drive and the switching motor drive;
    the transmission assembly having a gear assembly drivably coupled to the switching motor drive, the gear assembly configured to releasably engage at least one of the first rack member of the first cannula driver and the second rack member of the second cannula driver; and
    a coupler member connected to the linear motor drive, the coupler member configured to engage the flange of the first cannula driver.

2. The biopsy device of claim 1, the electrical controller circuit configured to execute program instructions to activate the switching motor drive to cause the gear assembly to selectively engage the first rack member of the first cannula driver and the second rack member of the second cannula driver, and configured to execute program instructions to activate the linear motor drive to move the coupler member along the longitudinal axis.

3. The biopsy device of claim 1, the electrical controller circuit configured to execute program instructions to activate the switching motor drive to cause the gear assembly to engage both of the first rack member of the first cannula driver and the second rack member of the second cannula driver, and configured to execute program instructions to activate the linear motor drive to move the coupler member in a proximal direction to retract both of the first cannula and the second cannula to a primed position when the gear assembly is engaged with both of the first rack member and the second rack member.

4. The biopsy device of claim 3, the electrical controller circuit configured to execute program instructions to activate the switching motor drive to cause the gear assembly to disengage from both of the first rack member of the first cannula driver and the second rack member of the second cannula driver, and configured to execute program instructions to activate the linear motor drive to move the coupler member in a distal direction to extend both of the first cannula and the second cannula to a pierce position.

5. The biopsy device of claim 4, the electrical controller circuit configured to execute program instructions to activate the switching motor drive to cause the gear assembly to be disengaged from the first rack member of the first cannula driver and to cause the gear assembly to engage with the second rack member of the second cannula driver, the gear assembly configured to lock the second cannula in the pierce position, and configured to execute program instructions to activate the linear motor drive to move the coupler member in a proximal direction to retract the first cannula relative to the second cannula to expose a sample notch in the second cannula.

6. The biopsy device of claim 5, further comprising a vacuum source in fluid communication with the sample notch, the electrical controller circuit configured to execute program instructions to activate the vacuum source as the first cannula is being retracted.

7. The biopsy device of claim 5, wherein with the gear assembly disengaged from the first rack member of the first cannula driver and engaged with the second rack member of the second cannula driver, the electrical controller circuit is configured to execute program instructions to activate the linear motor drive to move the coupler member in a distal direction to move the first cannula relative to the second cannula to cover the sample notch in the second cannula.

8. The biopsy device of claim 7, further comprising a vacuum source in fluid communication with a lumen of the second cannula, the electrical controller circuit configured to execute program instructions to activate the vacuum source as the first cannula is being moved.

9. The biopsy device of claim 1, wherein the power source includes a rechargeable battery electrically coupled to a capacitor storage bank, the capacitor storage bank being utilized to provide an increase of available power to the linear motor drive during a rapid extension of at least one of the first cannula and the second cannula.

10. The biopsy device of claim 1, wherein the drive assembly has a longitudinal axis that extends longitudinally through the transmission assembly, and wherein the transmission assembly includes a frame and a rack carriage slidably coupled to the frame and configured for linear translation along the longitudinal axis, the frame having a base defining a horizontal plane and a longitudinal plane that extends orthogonally upward from the horizontal plane, with a longitudinal extent of the longitudinal axis lying in the longitudinal plane.

11. The biopsy device of claim 10, wherein:
    the rack carriage has a body having a first exterior rack gear and a second exterior rack gear, the first exterior rack gear and the second exterior rack gear being located on opposite sides of the longitudinal plane, the body of the rack carriage having a first vertical slot and a second vertical slot, the first vertical slot and the second vertical slot being located in an interior of the rack carriage and located on opposite sides of and facing the longitudinal plane;
    the gear assembly including a first vertical rack gear slidably received in the first vertical slot and a second vertical rack gear slidably received in the second vertical slot, each of the first vertical rack gear and the second vertical rack gear having rack teeth that are spaced apart in a direction parallel to the longitudinal axis; and the switching motor drive including a first motor coupled to the first vertical rack gear and configured to selectively linearly translate the first vertical rack gear up and down in the first vertical slot of the rack carriage, such that the first vertical rack gear selectively engages the first rack member of the first cannula driver, and the switching motor drive including a second motor coupled to the second vertical rack gear and configured to selectively linearly translate the second vertical rack gear up and down in the second vertical slot of the rack carriage, such that the second vertical rack gear selectively engages the second rack member of the second cannula driver.

12. The biopsy device of claim 11, wherein:

the transmission assembly includes a first wing gear plate and a second wing gear plate, the first wing gear plate being pivotably coupled to the frame at a first pivot axis and the second wing gear plate being pivotably coupled to the frame at a second pivot axis, the first pivot axis and the second pivot axis being on opposite sides of the longitudinal plane, the first wing gear plate having a first linear gear and the second wing gear plate having a second linear gear;

a pivot linkage connected to each of the first wing gear plate and the second wing gear plate, the pivot linkage configured to engage the first linear gear with the first exterior rack gear of the rack carriage when the first wing gear plate is pivoted by the pivot linkage in a first rotational direction around the first pivot axis and to engage the second linear gear with the second exterior rack gear of the rack carriage when the second wing gear plate is pivoted by the pivot linkage in a second rotational direction around the second pivot axis, the first rotational direction being opposite to the second rotational direction; and the pivot linkage configured to disengage the first linear gear from the first exterior rack gear of the rack carriage when the first wing gear plate is pivoted by the pivot linkage in the second rotational direction around the first pivot axis and to disengage the second linear gear from the second exterior rack gear of the rack carriage when the second wing gear plate is pivoted by the pivot linkage in the first rotational direction around the second pivot axis; and the switching motor drive including a third motor drivably coupled to the pivot linkage.

13. The biopsy device of claim 12, wherein each of the first motor, the second motor and the third motor is a rotary motor.

14. The biopsy device of claim 10, further comprising a spring coupled between the frame and the rack carriage, the spring configured to bias the rack carriage toward a distal end of the frame.

15. A biopsy device, comprising:

a disposable needle assembly having a cutting cannula, a stylet, a cannula driver, and a stylet driver, the cannula driver connected to a first portion of the cutting cannula, the stylet driver being connected to a first portion of the stylet, the cannula driver having a first rack member and a flange connected to the first rack member, the stylet driver having a second rack member;

a linear motor drive having at least one linear motor;

a coupler member connected to the linear motor drive, the coupler member configured to engage the flange of the cannula driver of the disposable needle assembly;

a switching motor drive having at least one rotary motor;

a transmission assembly having a gear assembly drivably coupled to the switching motor drive, the gear assembly configured to releasably engage at least one of the first rack member of the cannula driver and the second rack member of the stylet driver; and an electrical controller circuit configured to execute program instructions to selectively operate the linear motor drive and the switching motor drive.

16. The biopsy device of claim 15, wherein the drive assembly has a longitudinal axis that extends longitudinally through the transmission assembly, the transmission assembly having a frame and a rack carriage slidably coupled to the frame and configured for linear translation along the longitudinal axis, the frame having a base defining a horizontal plane and a longitudinal plane that extends orthogonally upward from the horizontal plane, with a longitudinal extent of the longitudinal axis lying in the longitudinal plane.

17. The biopsy device of claim 16, wherein:

the rack carriage has a body having a first exterior rack gear and a second exterior rack gear, the first exterior rack gear and the second exterior rack gear being located on opposite sides of the longitudinal plane, the body of the rack carriage having a first vertical slot and a second vertical slot, the first vertical slot and the second vertical slot being located in an interior of the rack carriage and located on opposite sides of and facing the longitudinal plane;

the gear assembly including a first vertical rack gear slidably received in the first vertical slot and a second vertical rack gear slidably received in the second vertical slot, each of the first vertical rack gear and the second vertical rack gear having rack teeth that are spaced apart in a direction parallel to the longitudinal axis; and the switching motor drive including a first motor coupled to the first vertical rack gear and configured to selectively linearly translate the first vertical rack gear up and down in the first vertical slot of the rack carriage, such that the first vertical rack gear selectively engages the first rack member of the cannula driver, and the switching motor drive including a second motor coupled to the second vertical rack gear and configured to selectively linearly translate the second vertical rack gear up and down in the second vertical slot of the rack carriage, such that the second vertical rack gear selectively engages the second rack member of the stylet driver.

18. The biopsy device of claim 17, wherein:

the transmission assembly includes a first wing gear plate and a second wing gear plate, the first wing gear plate being pivotably coupled to the frame at a first pivot axis and the second wing gear plate being pivotably coupled to the frame at a second pivot axis, the first pivot axis and the second pivot axis being on opposite sides of the longitudinal plane, the first wing gear plate having a first linear gear and the second wing gear plate having a second linear gear;

a pivot linkage connected to each of the first wing gear plate and the second wing gear plate, the pivot linkage configured to simultaneously pivot the first wing gear plate in a first rotational direction around the first pivot axis and pivot the second wing gear plate in a second rotational direction around the second pivot axis, the first rotational direction being opposite to the second rotational direction, so as to simultaneously engage the first linear gear with the first exterior rack gear of the rack carriage and engage the second linear gear with the second exterior rack gear of the rack carriage, so as to lock a longitudinal position of the rack carriage to prevent movement of the rack carriage along the longitudinal axis; and the pivot linkage configured to simultaneously pivot first wing gear plate in the second rotational direction around the first pivot axis and pivot the second wing gear plate in the first rotational direction around the second pivot axis, so as to simultaneously disengage the first linear gear from the first exterior rack gear of the rack carriage and disengage the second linear gear from the second exterior rack gear of the rack carriage, so as to facilitate movement of the rack carriage along the longitudinal axis; and the switching motor drive including a third motor drivably coupled to the pivot linkage.

19. The biopsy device of claim 18, wherein each of the first motor, the second motor and the third motor is a rotary motor.

20. The biopsy device of claim 16, further comprising a spring coupled between the frame and the rack carriage, the spring configured to bias the rack carriage toward a distal end of the frame.

* * * * *